United States Patent
Du et al.

(10) Patent No.: US 9,493,502 B2
(45) Date of Patent: Nov. 15, 2016

(54) RIBOFURANOSYL PURINE COMPOUNDS, METHODS FOR PREPARING THE SAME AND USE THEREOF

(75) Inventors: Hongguang Du, Beijing (CN); Guocheng Liu, Beijing (CN); Zhongren Ding, Shanghai (CN); Shuming Wang, Beijing (CN)

(73) Assignee: Beijing KBD Pharmaceuticals Co., Ltd., Beijing (CN)

( * ) Notice: Subject to any disclaimer, the term of this patent is extended or adjusted under 35 U.S.C. 154(b) by 292 days.

(21) Appl. No.: 13/981,694

(22) PCT Filed: Jan. 20, 2012

(86) PCT No.: PCT/CN2012/000104
§ 371 (c)(1),
(2), (4) Date: Sep. 17, 2013

(87) PCT Pub. No.: WO2012/100654
PCT Pub. Date: Aug. 2, 2012

(65) Prior Publication Data
US 2014/0005138 A1 Jan. 2, 2014

(30) Foreign Application Priority Data
Jan. 26, 2011 (CN) .......................... 2011 1 0028107

(51) Int. Cl.
C07H 19/167 (2006.01)
A61K 31/7076 (2006.01)
C07H 19/16 (2006.01)

(52) U.S. Cl.
CPC ........... *C07H 19/16* (2013.01); *A61K 31/7076* (2013.01); *C07H 19/167* (2013.01)

(58) Field of Classification Search
None
See application file for complete search history.

(56) References Cited

U.S. PATENT DOCUMENTS

| 3,471,471 A | 10/1969 | Maguire | |
|---|---|---|---|
| 5,620,676 A | 4/1997 | Jacobson et al. | |
| 5,721,219 A * | 2/1998 | Ingall et al. | 514/47 |
| 5,955,447 A * | 9/1999 | Ingall | A61K 31/7076 514/47 |
| 2003/0007961 A1 | 1/2003 | Wilburn | |
| 2004/0110718 A1* | 6/2004 | Devos | C07H 19/16 514/45 |

FOREIGN PATENT DOCUMENTS

| CN | 1466591 A | 1/2004 |
|---|---|---|
| JP | 48 092397 A | 11/1973 |
| JP | S48-092397 | 11/1973 |
| JP | S49-110693 | 10/1974 |
| JP | H06-505987 A | 7/1994 |
| JP | H08-506335 A | 7/1996 |
| JP | 2004-513083 A | 4/2004 |
| JP | 2005-526046 A | 9/2005 |
| JP | 2008-512457 A | 4/2008 |
| WO | WO 92/17488 A1 | 10/1992 |
| WO | WO 94/18216 A1 | 8/1994 |
| WO | WO 95/02604 A1 | 1/1995 |
| WO | WO 02/18404 A2 | 3/2002 |
| WO | WO 03/072067 A2 | 9/2003 |

(Continued)

OTHER PUBLICATIONS

Fleysher et al., "N6-Substituted Adenosines: Synthesis, Biological Activity, and Some Structure-Activity Relationships" Jurnal of Medicinal Chemistry (1972) vol. 15 No. 2 pp. 187-191.*

(Continued)

*Primary Examiner* — Eric Olson
(74) *Attorney, Agent, or Firm* — Myers Bigel & Sibley, P.A.

(57) ABSTRACT

The present invention relates to the compounds of the formulae (I) and (I-1) and the process for preparing the same, uses of the compounds for the treatment of diseases associated with platelet aggregation and in the manufacture of a medicament for the treatment of diseases associated with platelet aggregation, and relates to a pharmaceutical composition and a pharmaceutical formulation containing the compounds, wherein the definitions of $R_1$, $R_2$, $R_3$ and $R_{2a}$ in the formulae are the same as those in the description.

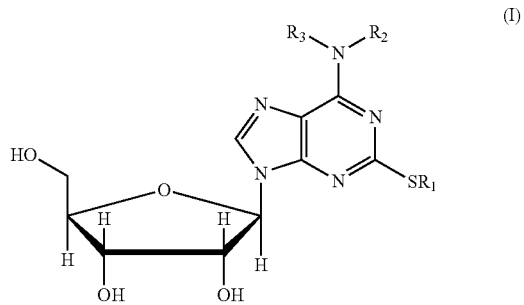

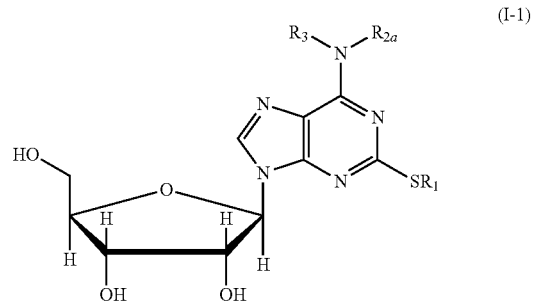

6 Claims, No Drawings

(56) References Cited

FOREIGN PATENT DOCUMENTS

| WO | WO 2004/058791 A2 | 7/2004 |
|----|-------------------|--------|
| WO | WO 2006/031505 A1 | 3/2006 |
| WO | WO 2010/130233 A1 | 11/2010 |

OTHER PUBLICATIONS

Burrows et al., "Isolation and Identification of Four Cytokinins from Wheat Germ Transfer Ribonucleic Acid" Biochemistry (1970) vol. 9 No. 9 pp. 1867-1872.*
Voller et al., "Anticancer activity of natural cytokinins: A structure-activity relationship study" Phytochemistry (2010) vol. 71 pp. 1350-1359.*
Hu et al., "BF061, a novel antiplatelet and antithrombotic agent targeting P2Y12 receptor and phosphodiesterase" Thrombosis and Haemostasis (2011) vol. 106 pp. 1203-1214.*
Schmitz et al., "Comparison of cytokinin activities of naturally occurring ribonucleosides and corresponding bases" Phytochemistry (1972) vol. 11 No. 5 pp. 1603-1610.*
Merriam-Webster's Collegiate Dictionary, Tenth Edition, published 1998 by Merriam-Webster, Incorporated, p. 924.*
Trivedi, "Studies Toward Synthesis of C2-Substituted Adenosines: An Efficient Synthesis of 2-(Phenylamino)Adenosine [CV-1808]" Nucleosides & Nucleotides (1988) vol. 7 No. 3 pp. 393-402.*
Trivedi et al., "C2,N6-Disubstituted Adenosines: Synthesis and Structure-Activity Relationships" Journal of Medicinal Chemistry (1989) vol. 32 pp. 1667-1673.*
Extended European Search Report corresponding to European Application No. 12739655.4 dated Jun. 3, 2014.
Bremond et al. "Stereoselective Synthesis of Novel Aristeromycin Analogues as Potential Antiviral Agents", *Synthesis*, 20:3253-3260, 2008.
Cattaneo M. "Advances in antiplatelet therapy: overview of new $P2Y_{12}$ receptor antagonists in development", *European Heart Journal Supplements*, 10 (Supplement I), 133-137, 2008.
Ingall et al. "Antagonists of the Platelet $P_{2T}$ Receptor: A Novel Approach to Antithrombotic Therapy", *J. Med. Chem.*, 1999, 42, 213-220.
Norgard et al. "Future Prospects in Anti-Platelet Therapy: A Review of Potential P2Y12 and Thrombin Receptor Antagonists", *Recent Patents on Cardiovascular Drug Discovery*, 2008, 3:194-200.

Zacharie et al. "2,6,9-Trisubstituted purine derivatives as protein A mimetics for the treatment of autoimmune diseases", *Bioorganic & Medicinal Chemistry Letters*, 19:242-246, 2009.
Gerster et al. "Purine Nucleosides. IV. The Synthesis of 6-Halogenated 9-β-D-Ribofuranosylpurines from Inosine and Guanosine[1]", *J. Organic Chem.* 28:945-948 (1963).
Ye et al. "Carba-nucleosides as Potent Antagonists of the Adenosine 5'-Diphosphate (ADP) Purinergic Receptor ($P2Y_{12}$) on Human Platelets", *ChemMedChem* 3(5):732-736 (2008).
Ingall et al. "Antagonists of the Platelet $P_{2T}$ Receptor: A Novel Approach to Antithrombotic Therapy", *J. Med. Chem.* 42:213-220 (1999).
Kierzek et al. "The synthesis of oligoribonucleotides containing $N^6$-alkyladenosines and 2-methylthio-$N^6$-alkyladenosines via post-synthetic modification of precursor oligomers", *Nucleic Acids Research* 31(15):4461-4471 (2003).
Kim et al. "2-Substitution of Adenine Nucleotide Analogues Containing a Bicyclo[3.1.0]hexane Ring System Locked in a Northern Conformation: Enhanced Potency as $P2Y_1$ Receptor Antagonists", *J. Med. Chem.* 46:4974-4987 (2003).
Matsuda et al. "Conversion of Guanosine into 2-Aminomethylinosine (2-Homoguanosine)", *Chem. Pharm. Bull.* 32(5):2048-2051 (1984).
Nair et al. "Selfone of the Antibiotic, Nebularine: Synthesis and Conversion to Novel Analogues of Nebularine", *Tetrahedron* 44(23):7001-7006 (1988).
Nair et al. "C-2 Functionalized $N^6$-Cyclosubstituted Adenosines: Highly Selective Agonists for the Adenosine $!_1$ Receptor", *Tetrahedron* 49(11):2169-2184 (1993).
Springthorpe et al. "From ATP to AZD6140: The discovery of an orally active reversible $P2Y_{12}$ receptor antagonist for the prevention of thrombosis", *Bioorganic & Medicinal Chemistry Letters* 17:6013-6018 (2007)
Tchilibon et al. "(N)-Methanocarba 2,$N_6$-Disubstituted Adenine Nucleosides as Highly Potent and Selective $A_3$ Adenosine Receptor Agonists", *J. Med. Chem.* 48(6):1745-1758 (2005).
Notice of Reasons for Rejection corresponding to Japanese Application No. 2013-550745 mailed Jan. 4, 2016.
Examination Report corresponding to European Application No. 12739655.4 dated Jul. 31, 2015.

* cited by examiner

RIBOFURANOSYL PURINE COMPOUNDS, METHODS FOR PREPARING THE SAME AND USE THEREOF

RELATED APPLICATIONS

This application is a 35 U.S.C. §371 national phase application of PCT Application PCT/CN2012/000104, filed Jan. 20, 2012, which claims priority to CN 201110028107.3, filed Jan. 26, 2011. The entire content of each of these applications is incorporated herein by reference.

TECHNICAL FIELD

The present invention relates to ribofuranosyl purine compounds, methods for preparing the same and use thereof in the manufacture of a medicament for the treatment of diseases associated with platelet aggregation. More specifically, the present invention relates to compounds having 9-β-D-ribofuranosyl purine as the parent structure, and comprising a substituted amino group at 6-position and a substituted hydrosulfuryl at 2-position, and relates to methods for preparing the same and use thereof for the treatment of diseases associated with platelet aggregation and in the manufacture of a medicament for the treatment of diseases associated with platelet aggregation, and relates to pharmaceutical compositions and formulations comprising said compounds.

BACKGROUND ART

Due to the biological importance of purine and the pharmacologists' studies on purine antineoplastic and antiviral medicines, purine chemistry develops rapidly. The research shows that purine compounds have important biological activities such as anti-viral, anti-cancer, blood pressure decreasing activities. The compounds prepared by using purine derivatives as the intermediates have special efficacy on cancers, AIDS, thrombosis and the like. The medicines such as from the earliest acyclovir to the lately developed ganciclovir, valganciclovir, abacavir, fludarabine and the like are widely and clinically applied (Bioorg. Med. Chem. Lett. 2009, 19, 242-246 and Synthesis 2008, 20, 3253-3260). In WO2004/058791A2, it is disclosed that 6-(substituted) benzylamino adenosine derivatives are thought to have anticancer, mitotic, immunosuppressive and antisenescent properties. In WO2010/130233A1, it is disclosed that 2-substituted-6-(substituted)benzylamino purine riboside derivatives are thought to have antiapoptotic, anti-inflammatory and differentiation activities.

Anthony H. Ingall et al. disclosed in 1994 (WO 94/18216) N-alkyl-2-substituted ATP analogues having the following formula, and methods for preparing the same,

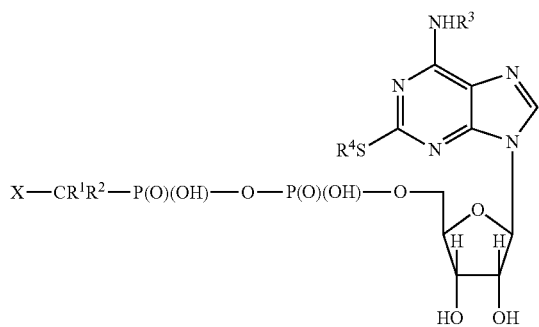

wherein $R^1$ and $R^2$ independently represent H or halogen; $R^3$ and $R^4$ independently represent phenyl or $C_{1-6}$ alkyl optionally substituted by one or more substitute(s) selected from the group consisting of $OR^5$, $C_{1-6}$ alkylthio, $NR^6R^7$, phenyl, $COOR^8$ and halogen; $R^5$, $R^6$, $R^7$ and $R^8$ independently represent H or $C_{1-6}$ alkyl; and X represents the acidic moiety. Such PCT application further provides the representative data of the in vitro anti-platelet aggregation activity test of the compounds, in which the tests were carried out by using human platelet treated with water. Anthony H. Ingall et al. further disclosed in 1999 a process for preparing 2-alkylthio-6-(alkyl)amino-5'-substituted-9-β-D-ribofuranosyl purine compounds (AR-C compounds) having the following formula

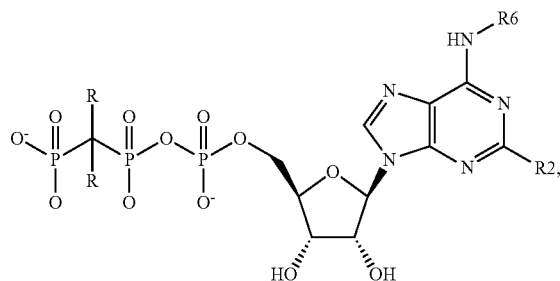

and the results of the activity measurement of ADP-induced platelet aggregation resistance carried out by using human platelet treated with water. The results show the above compounds have the activity of ADP-induced human platelet aggregation resistance (J. Med. Chem. 1999, 42, 213-220). The AR-C compound—Canrgelor is thought to have the advantages of high activity, fast effect, short half-life, reversibility, direct inhibition of platelet activation and the like (Eur. Heart. J. Suppl. 2008, 10, 133-137 and Recent Patents on Cardiovascular Drug Discovery, 2008, 3, 194-200), and has the prospect of being developed into a new class of antithrombotics medicines. Thus studies on the activity of anti-platelet aggregation of such 5'-substituted-9-β-D-ribofuranosyl purine compounds have become one of hotspots in the field of drug research.

However, the AR-C compounds have a complex structure, a longer synthesis routes, and a very tedious post-treatment process, in particular a biochemical reagent is required for introducing a substituted triphosphoric acid side chain into the 5'-position, and the said compounds have a bad oral availability. Thus there is an urgent need to develop a candidate medicine for anti-platelet aggregation having a simple structure, easy to synthesize, a better therapeutic effect and a lower side effect.

During the studies on the platelet aggregation inhibitors, the inventor of the present invention discovered a series of novel 2-substituted hydrosulfuryl-6-substituted amino-9-β-D-ribofuranosyl purine compounds having notable activity of anti-platelet aggregation and a simple structure, and measured the in vitro anti-platelet aggregation activity of the compounds, so as to achieve the present invention.

CONTENTS OF THE INVENTION

One object of the present invention is to provide a compound of the following formula (I) having the activity of anti-platelet aggregation, or a pharmaceutically acceptable salt thereof, as well as the uses thereof as platelet aggregation inhibitors or in the manufacture of a medicament for the treatment or prevention of diseases associated with platelet aggregation:

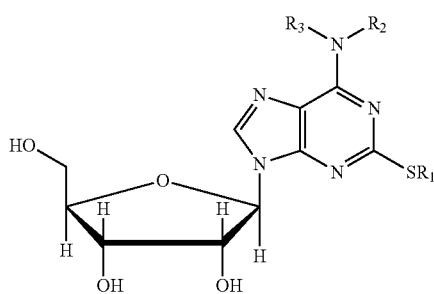

(I)

wherein:

$R_1$ represents an unsubstituted or $R_4$-substituted $C_1$-$C_8$ hydrocarbyl, or an unsubstituted or $R_5$-substituted 5- to 6-membered cyclic group;

$R_2$ represents an unsubstituted or $R_5$-substituted $C_3$-$C_8$ saturated or unsaturated aliphatic hydrocarbyl, an unsubstituted or $R_5$-substituted $C_3$-$C_8$ alicyclic group, an unsubstituted or $R_6$-substituted $C_6$-$C_{10}$ aryl-$C_1$-$C_4$ alkyl, an unsubstituted or $R_6$-substituted 5- to 10-membered heterocyclyl-$C_1$-$C_4$ alkyl, or an unsubstituted or $R_6$-substituted 5- to 10-membered heteroaryl-$C_1$-$C_4$ alkyl;

$R_3$ represents H or $R_2$;

$R_4$ represents halogen, $C_1$-$C_4$ alkyl, $C_1$-$C_4$ alkoxyl, halogenated $C_1$-$C_4$ alkyl, halogenated $C_1$-$C_4$ alkoxyl, hydroxyl, hydroxyl $C_1$-$C_4$ alkyl, carboxyl, nitro, cyano, $C_1$-$C_4$ alkylthio, or $C_1$-$C_4$ alkyl-CO—;

$R_5$ represents $C_1$-$C_4$ alkyl, $C_1$-$C_4$ alkoxyl, hydroxyl, hydroxyl $C_1$-$C_4$ alkyl, carboxyl, nitro, cyano, $C_1$-$C_4$ alkylthio or $C_1$-$C_4$ alkyl-CO—; and $R_6$ represents halogen, $C_1$-$C_4$ alkyl, $C_1$-$C_4$ alkoxyl, hydroxyl, hydroxyl $C_1$-$C_4$ alkyl, carboxyl, nitro, cyano, $C_1$-$C_4$ alkylthio, or $C_1$-$C_4$ alkyl-CO—.

Another object of the present invention is to provide a novel compound of the formula (I) having the structure of the following formula (I-1), or a pharmaceutically acceptable salt thereof:

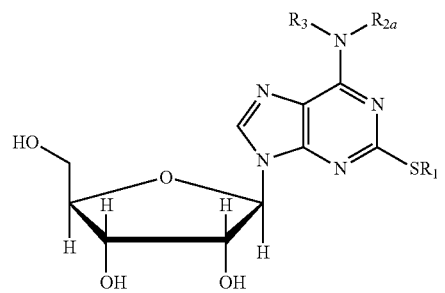

(I-1)

wherein $R_1$ represents an unsubstituted or $R_4$-substituted $C_1$-$C_8$ hydrocarbyl, or an unsubstituted or $R_5$-substituted 5- to 6-membered cyclic group;

$R_{2a}$ represents an unsubstituted or $R_5$-substituted $C_3$-$C_8$ saturated or unsaturated aliphatic hydrocarbyl, an unsubstituted or $R_5$-substituted $C_3$-$C_8$ alicyclic group, an unsubstituted or $R_6$-substituted $C_6$-$C_{10}$ aryl-$C_2$-$C_4$ alkyl, an unsubstituted or $R_6$-substituted 5- to 10-membered heterocyclyl-$C_1$-$C_4$ alkyl, or an unsubstituted or $R_6$-substituted 5- to 10-membered heteroaryl-$C_1$-$C_4$ alkyl;

$R_3$ represents H or $R_{2a}$;

$R_4$ represents halogen, $C_1$-$C_4$ alkyl, $C_1$-$C_4$ alkoxyl, halogenated $C_1$-$C_4$ alkyl, halogenated $C_1$-$C_4$ alkoxyl, hydroxyl, hydroxyl $C_1$-$C_4$ alkyl, carboxyl, nitro, cyano, $C_1$-$C_4$ alkylthio, or $C_1$-$C_4$ alkyl-CO—;

$R_5$ represents $C_1$-$C_4$ alkyl, $C_1$-$C_4$ alkoxyl, hydroxyl, hydroxyl $C_1$-$C_4$ alkyl, carboxyl, nitro, cyano, $C_1$-$C_4$ alkylthio or $C_1$-$C_4$ alkyl-CO—; and $R_6$ represents halogen, $C_1$-$C_4$ alkyl, $C_1$-$C_4$ alkoxyl, hydroxyl, hydroxyl $C_1$-$C_4$ alkyl, carboxyl, nitro, cyano, alkylthio, or $C_1$-$C_4$ alkyl-CO—;

provided that when $R_1$ is —$CH_3$ and $R_3$ is H, $R_{2a}$ is not cyclobutyl, cyclopentyl, cyclohexyl, cycloheptyl, decalinyl, 3-methyl-2-pentenyl, 2-methyl-3-hydroxyl-1-propenyl, 3-methyl-4-hydroxyl-1-butenyl, furfurylmethylene, 3-methyl-1-butenyl, 3-methyl-2-butenyl, 3-methylbutyl, 3-methyl-4-hydroxylbutyl, 3-methyl-4-hydroxyl-2-butenyl or 3-methyl-4-hydroxyl-3-butenyl; and when $R_1$ is propyl, $R_{2a}$ is not cyclopentyl, isopropyl, n-propyl or n-butyl.

Another object of the present invention is to provide a process for preparing the compound of the formula (I) (including the compound of the formula (I-1) (when $R_2$=$R_{2a}$ in the formula (I))), comprising using guanosine 1 as the starting material, firstly conducting the conventional esterification protection of three hydroxyl groups on the ribose ring of guanosine with anhydride or acyl halide, for example, acyl chloride, then halogenating the isomerized hydroxyl group at 6-position (using the conventional halogenating reagent, such as phosphorus oxyhalide $POX_3$)) to obtain 2-amino-6-halogenated-9-(2',3',5'-tri-O-acetyl-β-D-ribofuranosyl) purine 3, then diazotizing the amino at 2-position of 3 under the anhydrous condition (with the conventional diazotization reagents, such as isoamyl nitrite and the like), and then reacting with disulfide to obtain the corresponding 2-alkylthio-6-halogenated-9-(2',3',5'-tri-O-acetyl-β-D-ribofuranosyl) purine 4, and eventually conducting the nucleophilic substitution reaction with amine under the action of alkaline, and removing the protecting group by the catalysis with organic bases, e.g. alkali metal alkoxides such as sodium, potassium methoxide, sodium ethoxide or potassium ethoxide, to obtain the final product 2-substituted hydrosulfuryl-6-substituted amino-9-β-D-ribofuranosyl purine compound of the formula (I) or (I-1) (when $R_2$=$R_{2a}$ in the formula (I)). Such synthetic process has a simple operation, less reaction steps and a relatively higher yield. The synthetic route is shown as follows:

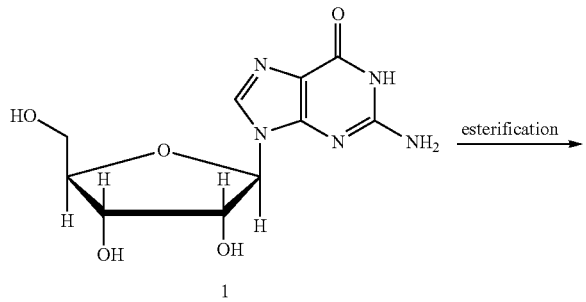

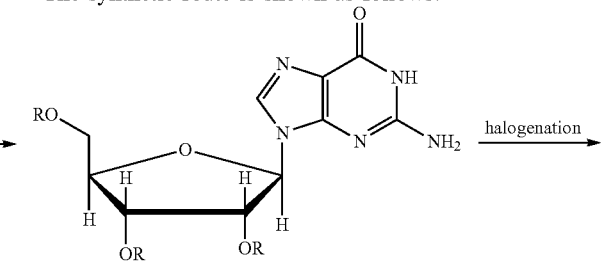

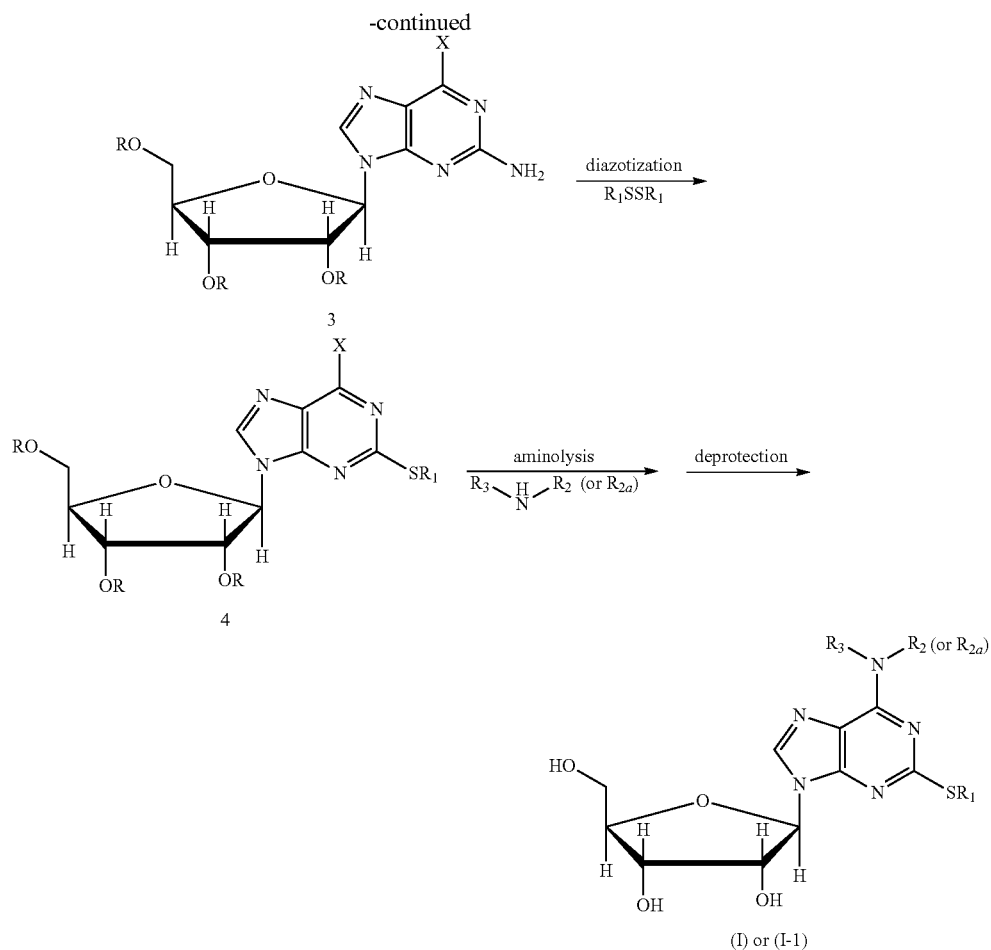

wherein R is acyl; X is halogen; $R_1$, $R_2$, $R_{2a}$ and $R_3$ are as defined in the compound of the above formula (I) or (I-1).

Another object of the present invention is to provide a pharmaceutical composition and formulation comprising the compound of the formula (I) (including the compound of the formula (I-1) (when $R_2=R_{2a}$ in the formula (I))) or a pharmaceutically acceptable salt thereof.

Another object of the present invention is to provide the use of the compound of the formula (I) (including the compound of the formula (I-1) (when $R_2=R_{2a}$ in the formula (I))) or a pharmaceutically acceptable salt thereof in the manufacture of a medicament for the treatment or prevention of diseases associated with platelet aggregation.

Another object of the present invention is to provide a method for the treatment or prevention of diseases associated with platelet aggregation, including administering an effective amount for the treatment or prevention of the compound of the formula (I) (including the compound of the formula (I-1) (when $R_2=R_{2a}$ in the formula (I))) or a pharmaceutically acceptable salt thereof to a mammal who needs it.

In the present invention, the term "$C_1$-$C_8$ hydrocarbyl" represents a linear or branched, saturated or unsaturated hydrocarbyl having 1 to 8 carbon atoms, comprising $C_1$-$C_8$ linear or branched alkyl, $C_1$-$C_8$ linear or branched alkenyl and $C_1$-$C_8$ linear or branched alkynyl, e.g. methyl, ethyl, propyl, isopropyl, n-butyl, isobutyl, tert-butyl, n-amyl, iso-amyl, neopentyl, n-hexyl, 2-methylpentyl, 3-methylpentyl, 2,3-dimethylbutyl, 2-methylhexyl, 3-methylhexyl, 2,3-dimethylpentyl, 2,2,3-trimethylbutyl, 2,3,3-trimethylbutyl, n-heptyl, 2-methylheptyl, 3-methylheptyl, 4-methylheptyl, 3-ethylhexyl, 2,3-dimethylhexyl, 2,4-dimethylhexyl, 2,5-dimethylhexyl, n-octyl, allyl, 2-butenyl, 2-pentenyl, 2-hexenyl, 3-hexenyl, 2-heptenyl, 3-heptenyl, 2-octenyl, 3-octenyl, 4-octenyl, propargyl, 2-butynyl, 2-pentynyl, 2-hexynyl, 3-hexynyl, 2-heptynyl, 3-heptynyl, 2-octynyl, 3-octynyl, 4-octynyl and the like, wherein $C_1$-$C_6$ hydrocarbyl is preferred.

The term "5- to 6-membered cyclic group" represents 5- to 6-membered, saturated or unsaturated alicyclic non-aromatic carbon ring group or 5- to 6-membered, saturated or unsaturated heterocyclyls, wherein said heterocyclyls comprise heteroatoms selected from the group consisting of N, O and S; 6-membered cyclic group is particularly preferred. Said cyclic group includes, but is not limited to, e.g. cyclopentyl, cyclohexyl, cyclopentenyl, cyclohexenyl, pyrrolidinyl, imidazolidinyl, pyrazolidinyl tetrahydrofuryl, tetrahydrothiophenyl, tetrahydropyranyl, oxazolidinyl, pyrrolyl, dihydropyrrolyl, imidazolyl, dihydroimidazolyl, pyrazolyl, dihydropyrazolyl, pyridyl, pyridazinyl, pyrimidinyl, pyrazinyl, furyl, dihydrofuryl, thienyl, dihydrothienyl, pyranyl, dihydropyranyl, oxazolyl, dihydrooxazolyl, isoxazolyl, dihydroisoxazolyl, thiazolyl, dihydrothiazolyl, isothiazolyl and the like.

In the present invention, the term "$C_3$-$C_8$ saturated or unsaturated aliphatic hydrocarbyl group" represents a linear or branched, saturated or unsaturated hydrocarbyl having 3 to 8 carbon atoms, including $C_3$-$C_8$ linear or branched alkyl group, $C_3$-$C_8$ linear or branched alkenyl and $C_3$-$C_8$ linear or branched alkynyl. Said hydrocarbyl group includes, but is not limited to, e.g. propyl, isopropyl, n-butyl, isobutyl, tert-butyl, n-amyl, isoamyl, neopentyl, n-hexyl, 2-methylpentyl, 3-methylpentyl, 2,3-dimethylbutyl, 2-methylhexyl, 3-methylhexyl, 2,3-dimethyl pentyl, 2,2,3-trimethylbutyl, 2,3,3-trimethylbutyl, n-heptyl, 2-methylheptyl, 3-methylheptyl, 4-methylheptyl, 3-ethylhexyl, 2,3-dimethylhexyl, 2,4-dimethylhexyl, 2,5-dimethylhexyl, n-octyl, allyl, isopropenyl, 2-butenyl, 2-pentenyl, 2-hexenyl, 3-hexenyl, 2-heptenyl, 3-heptenyl, 2-octenyl, 3-octenyl, 4-octenyl, propargyl, 2-butynyl, 2-pentynyl, 2-hexynyl, 3-hexynyl, 2-heptynyl, 3-heptynyl, 2-octynyl, 3-octynyl, 4-octynyl and the like.

In the present invention, the term "$C_3$-$C_8$ alicyclic group" represents 3- to 8-membered saturated or unsaturated alicyclic carbon ring group, and the said group includes, but is not limited to, e.g. cyclopropyl, cyclobutyl, cyclopentyl, cyclohexyl, cycloheptyl, cyclooctyl, cyclopentenyl, cyclohexenyl and the like.

In the present invention, the term "$C_6$-$C_{10}$ aryl" represents 6- to 10-membered, aromatic, monocyclic or bicyclic carbon ring group, wherein one ring of the bicyclic carbon ring group may be hydrogenated, includes, e.g. phenyl, naphthyl, dihydronaphthyl, tetrahydronaphthyl and the like.

Said "$C_6$-$C_{10}$ aryl-$C_1$-$C_4$ alkyl" includes, but is not limited to, e.g. benzyl, phenylethyl, phenylpropyl, phenylisopropyl, phenylbutyl, phenyl isobutyl, phenyl t-butyl, menaphthyl, naphthylethyl, naphthylpropyl, naphthylbutyl, dihydromenaphthyl, dihydronaphthylethyl, dihydronaphthylpropyl, dihydronaphthylbutyl, tetrahydromenaphthyl, tetrahydronaphthylethyl, tetrahydronaphthylpropyl, tetrahydronaphthylbutyl and the like.

In the present invention, the term "5- to 10-membered heterocyclyl" represents 5- to 10-membered, monocyclic or bicyclic, alicyclic heterocyclyl containing heteroatoms selected from the group consisting of N, O and S. Said heterocyclyl includes, but is not limited to, tetrahydrofuryl, tetrahydrothienyl, 1,3-dioxolanyl, 1,3-dithiolanyl, tetrahydropyranyl, 1,4-dioxanyl, 1,3-dioxanyl, 1,3-oxathianyl, dihydrofuryl, dihydrothienyl, dihydropyranyl, dihydrooxazolyl, dihydrothiazolyl and the like.

In the present invention, the term "5- to 10-membered heteroaryl group" represents 5- to 10-membered, aromatic, monocyclic or bicyclic heterocyclyl containing heteroatoms selected from the group consisting of N, O and S. Said heteroaryl group includes, but is not limited to, e.g. pyridyl, pyridazinyl, pyrimidinyl, pyrazinyl, furyl, imidazolyl, pyranyl, pyrazolyl, oxazolyl, isooxazolyl, thiazolyl, isothiazolyl, thienyl, purinyl, benzofuranyl, benzothiophenyl, diazinyl, isobenzothiophenyl, isobenzofuranyl, indolyl, isoindolyl, quinolinyl, isoquinolinyl and the like.

In the present invention, the term "halogen" represents fluorine, chlorine, bromine, iodine.

In the present invention, the term "pharmaceutically acceptable salt" represents a salt formed by reacting a pharmaceutically acceptable nontoxic acid with the alkaline moiety of the compound of the formula (I) or (I-1) of the present invention, including, e.g. hydrochlorides, acetates, hydrobromides, sulfates, bisulfates, carbonates, bicarbonates, sulfites, phosphates, biphosphates, oxalates, malonates, pentanoate, borates, p-toluene sulphonates, mesylates, tartrates, benzoates, lactates, citrates, maleates, fumarates, malates, salicylates, amygdalates, succinates, gluconates, lactobionates and the like. Such salt may be prepared by the method well known by those skilled in the art.

In one embodiment of the compound of the formula (I) or (I-1) of the present invention, $R_3$ represents H or $C_3$-$C_6$ alkyl.

In one preferred embodiment of the compound of the formula (I) or (I-1) of the present invention, $R_1$ represents an unsubstituted or $R_4$-substituted $C_1$-$C_6$ alkyl, wherein $R_4$ represents halogen, $C_1$-$C_4$ alkyl, $C_1$-$C_4$ alkoxyl, halogenated $C_1$-$C_4$ alkyl, halogenated $C_1$-$C_4$ alkoxyl, hydroxyl, hydroxyl $C_1$-$C_4$ alkyl, carboxyl, nitro, cyano, $C_1$-$C_4$ alkylthio, $C_1$-$C_4$-alkyl-CO—.

In one preferred embodiment of the compound of the formula (I) of the present invention, $R_2$ represents an unsubstituted or $R_5$-substituted $C_3$-$C_8$, preferably $C_3$-$C_6$ alkyl, an unsubstituted or $R_5$-substituted $C_3$-$C_6$ cycloalkyl, an unsubstituted or $R_6$-substituted phenyl-$C_1$-$C_4$ alkyl, an unsubstituted or $R_6$-substituted 5- to 6-membered heteroaryl-$C_1$-$C_4$ alkyl, or an unsubstituted or $R_6$-substituted 5- to 6-membered heterocyclyl-$C_1$-$C_4$ alkyl, wherein $R_5$ is selected from the group consisting of $C_1$-$C_4$ alkyl, $C_1$-$C_4$ alkoxyl, hydroxyl, hydroxyl $C_1$-$C_4$ alkyl, carboxyl, nitro, cyano, $C_1$-$C_4$ alkylthio and $C_1$-$C_4$ alkyl-CO—; and $R_6$ is selected from the group consisting of halogen, $C_1$-$C_4$ alkyl, $C_1$-$C_4$ alkoxyl, hydroxyl, hydroxyl $C_1$-$C_4$ alkyl, carboxyl, nitro, cyano, $C_1$-$C_4$ alkylthio and $C_1$-$C_4$ alkyl-CO—.

In one preferred embodiment of the compound of the formula (I-1) of the present invention, $R_{2a}$ represents an unsubstituted or $R_5$-substituted $C_3$-$C_8$, preferably $C_3$-$C_6$ alkyl, an unsubstituted or $R_5$-substituted $C_3$-$C_6$ cycloalkyl, an unsubstituted or $R_6$-substituted phenyl-$C_2$-$C_4$ alkyl, an unsubstituted or $R_6$-substituted 5- to 6-membered heteroaryl-$C_1$-$C_4$ alkyl, or an unsubstituted or $R_6$-substituted 5- to 6-membered heterocyclyl-$C_1$-$C_4$ alkyl, wherein $R_5$ is selected from the group consisting of $C_1$-$C_4$ alkyl, $C_1$-$C_4$ alkoxyl, hydroxyl, hydroxyl $C_1$-$C_4$ alkyl, carboxyl, nitro, cyano, $C_1$-$C_4$ alkylthio and $C_1$-$C_4$ alkyl-CO—; and $R_6$ is selected from the group consisting of halogen, $C_1$-$C_4$ alkyl, $C_1$-$C_4$ alkoxyl, hydroxyl, hydroxyl $C_1$-$C_4$ alkyl, carboxyl, nitro, cyano, $C_1$-$C_4$ alkylthio and $C_1$-$C_4$ alkyl-CO—.

In one preferred embodiment of the compound of the formula (I) of the present invention, $R_1$ represents an unsubstituted or $R_4$-substituted $C_1$-$C_6$ alkyl; $R_2$ represents an unsubstituted or $R_5$-substituted $C_3$-$C_6$ alkyl, an unsubstituted or $R_5$-substituted $C_3$-$C_6$ cycloalkyl, an unsubstituted or $R_6$-substituted 5- to 6-membered heteroaryl-$C_1$-$C_4$ alkyl, an unsubstituted or $R_6$-substituted phenyl-$C_1$-$C_4$ alkyl, or an unsubstituted or $R_6$-substituted 5- to 6-membered heterocyclyl-$C_1$-$C_4$ alkyl; and $R_3$ represents H or $C_3$-$C_6$ alkyl; wherein $R_4$ represents halogen, $C_1$-$C_4$ alkyl, $C_1$-$C_4$ alkoxyl, halogenated $C_1$-$C_4$ alkyl, halogenated $C_1$-$C_4$ alkoxyl, hydroxyl, hydroxyl $C_1$-$C_4$ alkyl, carboxyl, nitro, cyano, $C_1$-$C_4$ alkylthio, $C_1$-$C_4$-alkyl-CO—; $R_5$ is selected from the group consisting of $C_1$-$C_4$ alkyl, $C_1$-$C_4$ alkoxyl, hydroxyl, hydroxyl $C_1$-$C_4$ alkyl, carboxyl, nitro, cyano, $C_1$-$C_4$ alkylthio and $C_1$-$C_4$ alkyl-CO—; and $R_6$ is selected from the group consisting of halogen, $C_1$-$C_4$ alkyl, $C_1$-$C_4$ alkoxyl, hydroxyl, hydroxyl $C_1$-$C_4$ alkyl, carboxyl, nitro, cyano, $C_1$-$C_4$ alkylthio and $C_1$-$C_4$ alkyl-CO—.

In one preferred embodiment of the compound of the formula (I-1) of the present invention, $R_1$ represents an unsubstituted or $R_4$-substituted $C_1$-$C_6$ alkyl; $R_{2a}$ represents an unsubstituted or $R_5$-substituted $C_3$-$C_6$ alkyl, an unsubstituted or $R_5$-substituted $C_3$-$C_6$ cycloalkyl, an unsubstituted or $R_6$-substituted 5- to 6-membered heteroaryl-$C_1$-$C_4$ alkyl, an unsubstituted or $R_6$-substituted phenyl-$C_2$-$C_4$ alkyl, or an unsubstituted or $R_6$-substituted 5- to 6-membered heterocyclyl-$C_1$-$C_4$ alkyl; and $R_3$ represents H or $C_3$-$C_6$ alkyl; wherein $R_4$ represents halogen, $C_1$-$C_4$ alkyl, $C_1$-$C_4$ alkoxyl, halogenated $C_1$-$C_4$ alkyl, halogenated $C_1$-$C_4$ alkoxyl, hydroxyl, hydroxyl $C_1$-$C_4$ alkyl, carboxyl, nitro, cyano, $C_1$-$C_4$ alkylthio, or $C_1$-$C_4$-alkyl-CO—; $R_5$ is selected from the group consisting of $C_1$-$C_4$ alkyl, $C_1$-$C_4$ alkoxyl, hydroxyl, hydroxyl $C_1$-$C_4$ alkyl, carboxyl, nitro, cyano, alkylthio and $C_1$-$C_4$ alkyl-CO—; and $R_6$ is selected from the group consisting of halogen, $C_1$-$C_4$ alkyl, $C_1$-$C_4$ alkoxyl, hydroxyl, hydroxyl $C_1$-$C_4$ alkyl, carboxyl, nitro, cyano, $C_1$-$C_4$ alkylthio and $C_1$-$C_4$ alkyl-CO—.

In another preferred embodiment of the compound of the formula (I) of the present invention, $R_1$ represents $C_1$-$C_6$ alkyl; $R_2$ represents $C_3$-$C_6$ alkyl, $C_5$-$C_6$ cycloalkyl, an unsubstituted or $R_6$-substituted phenyl-$C_1$-$C_4$ alkyl, an unsubstituted or $R_6$-substituted 5- to 6-membered heteroaryl-$C_1$-$C_4$ alkyl, or an unsubstituted or $R_6$-substituted 5- to 6-membered heterocyclyl-$C_1$-$C_4$ alkyl, wherein $R_6$ is selected from the group consisting of halogen, $C_1$-$C_4$ alkyl, $C_1$-$C_4$ alkoxyl, hydroxyl, hydroxyl $C_1$-$C_4$ alkyl and $C_1$-$C_4$ alkylthio.

In another preferred embodiment of the compound of the formula (I-1) of the present invention, $R_1$ represents $C_1$-$C_6$ alkyl; $R_{2a}$ represents $C_3$-$C_6$ alkyl, $C_5$-$C_6$ cycloalkyl, an unsubstituted or $R_6$-substituted phenyl-$C_2$-$C_4$ alkyl, an unsubstituted or $R_6$-substituted 5- to 6-membered heteroaryl-$C_1$-$C_4$ alkyl, or an unsubstituted or $R_6$-substituted 5- to 6-membered heterocyclyl-$C_1$-$C_4$ alkyl, wherein $R_6$ is selected from the group consisting of halogen, $C_1$-$C_4$ alkyl, $C_1$-$C_4$ alkoxyl, hydroxyl, hydroxyl $C_1$-$C_4$ alkyl and $C_1$-$C_4$ alkylthio.

In another preferred embodiment of the compound of the formula (I) of the present invention, $R_1$ represents $C_1$-$C_4$ alkyl; $R_2$ represents $C_3$-$C_6$ alkyl, $C_5$-$C_6$ cycloalkyl, or $C_1$-$C_4$ alkyl-substituted or $C_1$-$C_4$ alkoxyl-substituted phenyl-$C_1$-$C_4$ alkyl, unsubstituted or $C_1$-$C_4$ alkyl-substituted or $C_1$-$C_4$ alkoxyl-substituted 5- to 6-membered heteroaryl-$C_1$-$C_4$ alkyl, or unsubstituted or $C_1$-$C_4$ alkyl-substituted or $C_1$-$C_4$ alkoxyl-substituted 5- to 6-membered heterocyclyl-$C_1$-$C_4$ alkyl; and $R_3$ represents H or $C_3$-$C_4$ alkyl.

In another preferred embodiment of the compound of the formula (I-1) of the present invention, $R_1$ represents $C_1$-$C_4$ alkyl; $R_{2a}$ represents $C_4$-$C_6$ alkyl, $C_5$-$C_6$ cycloalkyl, $C_1$-$C_4$ alkyl-substituted or $C_1$-$C_4$ alkoxyl-substituted phenyl-$C_2$-$C_4$ alkyl, unsubstituted or $C_1$-$C_4$ alkyl-substituted or $C_1$-$C_4$ alkoxyl-substituted 5- to 6-membered heteroaryl-$C_1$-$C_4$ alkyl, or unsubstituted or $C_1$-$C_4$ alkyl-substituted or $C_1$-$C_4$ alkoxyl-substituted 5- to 6-membered heterocyclyl-$C_1$-$C_4$ alkyl; and $R_3$ represents H or $C_3$-$C_4$ alkyl.

In another preferred embodiment of the compound of the formula (I) of the present invention, $R_1$ represents methyl, ethyl, n-propyl, isopropyl or butyl; $R_2$ represents n-hexyl, cyclohexyl, 1-phenylethyl, 2-phenylethyl, 3-phenylpropyl, 4-phenylbutyl, methoxylphenylethyl, 2-thienylethyl, furylmethyl, or tetrahydrofurylmethyl; and $R_3$ represents H or $C_3$-$C_4$ alkyl.

In another preferred embodiment of the compound of the formula (I-1) of the present invention, $R_1$ represents methyl, ethyl, n-propyl, isopropyl or butyl; $R_{2a}$ represents n-hexyl, cyclohexyl, 2-phenylethyl, 3-phenylpropyl, 4-phenylbutyl, methoxylphenylethyl, 2-thienylethyl, furylmethyl, or tetrahydrofurylmethyl; and $R_3$ represents H or $C_3$-$C_4$ alkyl.

The particularlly preferred compounds of the formula (I) or (I-1) (when $R_2=R_{2a}$ in the formula (I)) of the present invention comprise the following compounds and pharmaceutically acceptable salts thereof:

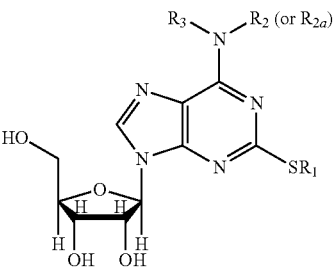

| Name of compounds | $R_1$ | $R_2$ or $R_{2a}$ | $R_3$ |
|---|---|---|---|
| 2-propylthio-6-n-hexylamino-9-β-D-ribofuranosyl purine | propyl | n-hexyl | H |
| 2-ethylthio-6-cyclohexylamino-9-β-D-ribofuranosyl purine | ethyl | cyclohexyl | H |
| 2-propylthio-6-cyclohexylamino-9-β-D-ribofuranosyl purine | propyl | cyclohexyl | H |
| 2-isopropylthio-6-cyclohexylamino-9-β-D-ribofuranosyl purine | isopropyl | cyclohexyl | H |
| 2-butylthio-6-cyclohexylamino-9-β-D-ribofuranosyl purine | butyl | cyclohexyl | H |
| 2-ethylthio-6-benzylamino-9-β-D-ribofuranosyl purine | ethyl | benzyl | H |
| 2-propylthio-6-benzylamino-9-β-D-ribofuranosyl purine | propyl | benzyl | H |
| 2-butylthio-6-benzylamino-9-β-D-ribofuranosyl purine | butyl | benzyl | H |
| 2-ethylthio-6-(1-phenylethyl)amino-9-β-D-ribofuranosyl purine | ethyl | 1-phenylethyl | H |
| 2-propylthio-6-([4-methoxylbenzyl]-amino)-9-β-D-ribofuranosyl purine | propyl | 4-methoxyl-benzyl | H |
| 2-methylthio-6-phenylethylamino-9-β-D-ribofuranosyl purine | methyl | phenylethyl | H |
| 2-ethylthio-6-phenylethylamino-9-β-D-ribofuranosyl purine | ethyl | phenylethyl | H |
| 2-propylthio-6-phenylethylamino-9-β-D-ribofuranosyl purine | propyl | phenylethyl | H |
| 2-butylthio-6-phenylethylamino-9-β-D-ribofuranosyl purine | butyl | phenylethyl | H |
| 2-methylthio-6-([4-methoxylphenylethyl]-amino)-9-β-D-ribofuranosyl purine | methyl | 4-methoxyl-phenylethyl | H |
| 2-ethylthio-6-([4-methoxylphenylethyl]-amino)-9-β-D-ribofuranosyl purine | ethyl | 4-methoxyl-phenylethyl | H |
| 2-propylthio-6-([4-methoxylphenylethyl]-amino)-9-β-D-ribofuranosyl purine | propyl | 4-methoxyl-phenylethyl | H |
| 2-butylthio-6-([4-methoxylphenylethyl]-amino)-9-β-D-ribofuranosyl purine | butyl | 4-methoxyl-phenylethyl | H |
| 2-ethylthio-6-([3-methoxylphenylethyl]-amino)-9-β-D-ribofuranosyl purine | ethyl | 3-methoxyl-phenylethyl | H |
| 2-propylthio-6-([3-methoxylphenylethyl]amino)-9-β-D-ribofuranosyl purine | propyl | 3-methoxyl-phenylethyl | H |
| 2-ethylthio-6,6-(dibutylamino)-9-β-D-ribofuranosyl purine | ethyl | butyl | butyl |
| 2-ethylthio-6-(2-thienylethyl)amino-9-β-D-ribofuranosyl purine | ethyl | 2-thienylethyl | H |
| 2-propylthio-6-(2-thienylethyl)amino-9-β-D-ribofuranosyl purine | propyl | 2-thienylethyl | H |
| 2-ethylthio-6-(3-phenylpropyl)amino-9-β-D-ribofuranosyl purine | ethyl | 3-phenyl-propyl | H |
| 2-ethylthio-6-(4-phenylbutyl)amino-9-β-D-ribofuranosyl purine | ethyl | 4-phenyl-butyl | H |
| 2-ethylthio-6-(2-furylmethyl)amino-9-β-D-ribofuranosyl purine | ethyl | 2-furyl-methyl | H |
| 2-ethylthio-6-(2-tetrahydrofurylmethyl)-amino-9-β-D-ribofuranosyl purine | ethyl | 2-tetrahydro-furylmethyl | H |

In one embodiment of the process for preparing the compound of the general formula (I) or (I-1) (when $R_2=R_{2a}$ in the general formula (I)), the process may comprise the following specific steps:

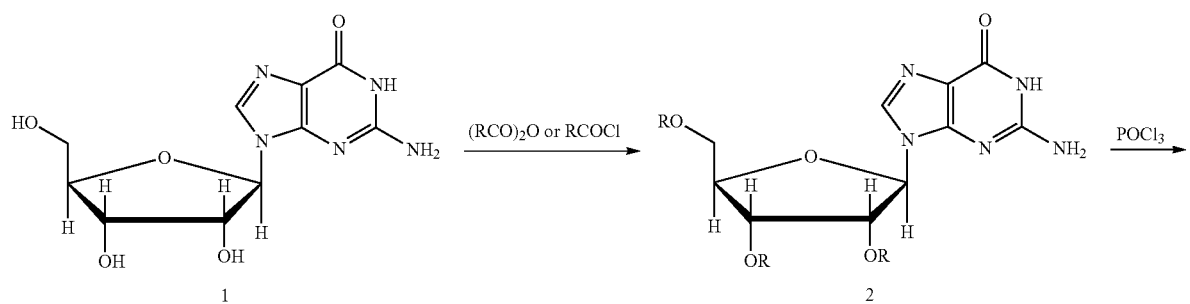

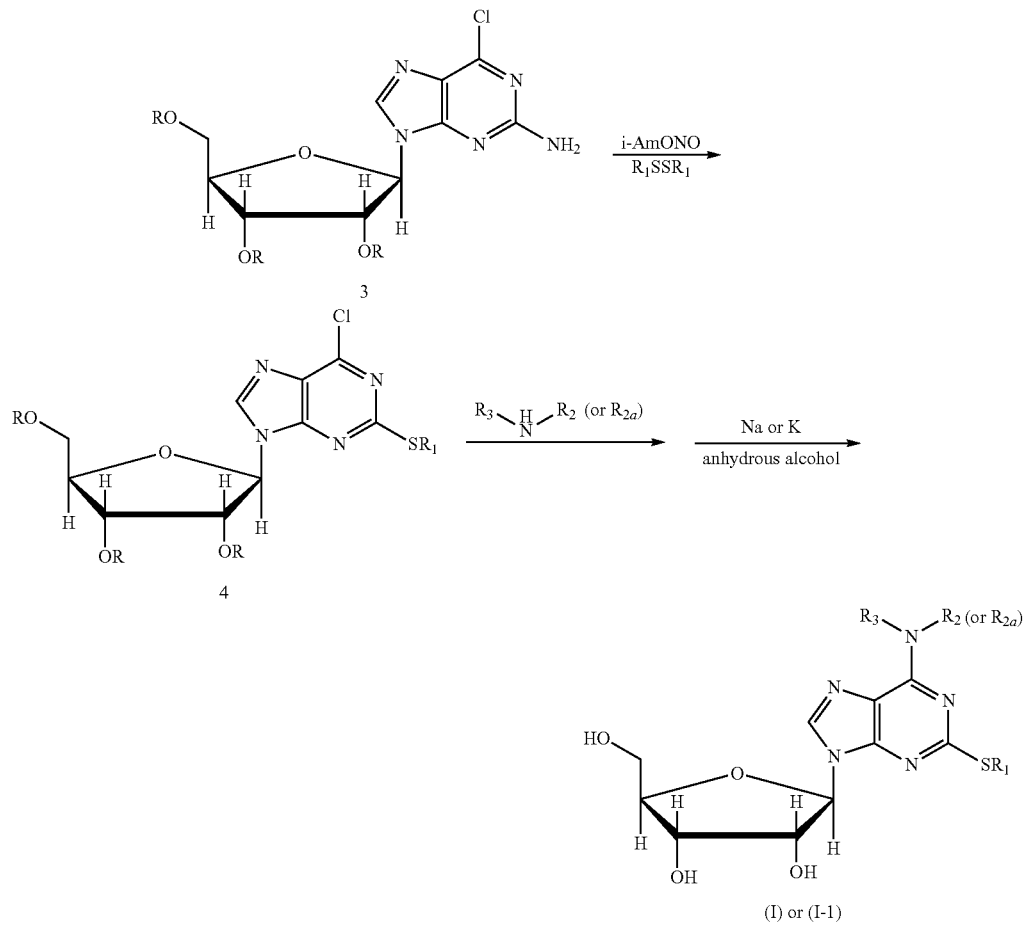

a) adding dried guanosine 1, acetic anhydride or acyl halide and organic base, such as triethylamine in an molar ratio of about 1:3.5:4 into anhydrous acetonitrile successively, upon being fully dissolved, adding to the solution 4-dimethylamino pyridine in a catalytic amount, sharply stirring at room temperature for 0.5 h, then evaporating the solvent under reduced pressure, and then recrystallizing the residue with isopropanol to obtain an intermediate 2;

b) successively adding the intermediate 2, anhydrous $Et_4NCl$, $POCl_3$ and N,N-dimethylaniline in an molar ratio of about 1:3:4.5:1.5 into a mixed solvent of anhydrous acetonitrile and anhydrous 1,2-dichloroethane in a volume ratio of 1:2, heating and refluxing the mixture for 20-25 min, then slowly pouring the resulting mixture into brash ice, on being fully dissolved, separating the liquid, extracting, and combining the obtained organic phases, adjusting the pH to about 7.0 with 5% sodium bicarbonate solution, re-separating the liquid and extracting, drying the organic phase, and then distilling the organic phase under reduced pressure, recrystallizing the residue with ethanol to obtain a white crystalline intermediate 3;

c) adding the intermediate 3 and the corresponding disulfide in a molar ratio of 1:5 into anhydrous acetonitrile successively, and then stirring the mixture at room temperature and feeding the protecting gas for about 20-30 min, to the reaction system immediately adding 6.2 mol of isoamyl nitrite (i-AmONO), continuously stirring, then reacting at 60-80° C. for 4-8 h, separating the resulting mixture by the silica gel column chromatography to obtain an intermediate 4;

d) successively adding the intermediate 4, the corresponding amine and organic base (e.g. triethylamine, sodium hydride, potassium tertbutoxide and the like) in a molar ratio of about 1:5:1 into an anhydrous alcohol, e.g. ethanol or methanol, heating and refluxing the mixture for 4-8 h, adding metal sodium or potassium in a catalytic amount after it is monitored by TLC that the starting materials disappear, continuously heating and refluxing the reaction mixture till it is monitored by TLC that the reaction is completed, and then evaporating the solvent under reduced pressure, separating the residue by the silica gel column chromatography neutralized with alkaline, recrystallizing to obtain the target product compound of the formula (I) or (I-1) (when $R_2=R_{2a}$ in the formula (I)).

It has been proved by tests that the compound of the formula (I) of the present invention has notable activities of anti-platelet aggregation, and can be used for the treatment and/or prevention of various diseases associated with platelet aggregation.

Thus the present invention further provides a pharmaceutical composition containing the compound of the formula (I-1) or a pharmaceutically acceptable salt thereof and a pharmaceutically acceptable carrier.

The pharmaceutically acceptable carrier may include the conventional pharmaceutically acceptable carriers in the art, e.g. fillers, binders, disintegrating agents, lubricants, solvents, solubilizers, substrates for transdermal patches, substrates for suppository and the like, including, but not limited to starch, powdered sugar, calcium phosphate, magnesium stearate, talc powder, dextrin, cellulose and derivatives thereof, microcrystalline cellulose, polyethylene glycol, normal saline, glucose solution, conventional substrates for transdermal patches such as acrylic pressure-sensitive adhesives, siloxane (silicone) pressure-sensitive adhesives, polyisobutylene pressure-sensitive adhesives or combinations thereof, cocoa butter, paraffin and the like.

The pharmaceutical composition of the present invention may also comprise various other common additives, e.g. preservatives, emulsifying agents, suspending agents, flavoring agents and the like.

The pharmaceutical composition of the present invention may be prepared as any suitable pharmaceutically acceptable dosage form, e.g. tablets, capsules, pills, granular formulations, syrups, injections, solutions, suspensions, transdermal patches, suppository and the like.

The compound of the formula (I) of the present invention or a pharmaceutically acceptable salt thereof may be administered to mammals, e.g. human beings, via any effective routes, including oral, intravenous, intraperitoneal, intramuscular, topical, transdermal, intraocular, intranasal, inhalation, subcutaneous, intramuscular, buccal, sublingual, rectal administration and the like. They may be administered alone, or in combination with other active ingredients. The compound of the formula (I) of the present invention or a pharmaceutically acceptable salt thereof is in an effective amount of from about 0.01 mg per kg weight per day (mg/kg/day) to about 100 mg/kg/day, e.g. from about 0.1 mg/kg/day to about 80 mg/kg/day. The preferred amount can be determined by those skilled in the art. For example, the doctors in charge can readily determine the effective amount by the conventional methods and by observing the results obtained under similar circumstances. While the effective amount of the compound of the present invention is determined, many factors should be taken into consideration by the doctors in charge, including, but not limited to specific compounds to be administered; combined administration with other pharmaceuticals; kind, size, age and general health condition of mammals; severity of the disease; response of individual patients; method of administration, bioavailability characteristics of the formulation to be administered; dose scheme to be selected; use of other concomitant drugs and other related situations.

The present invention further provides the use of the compound of the formula (I) of the present invention in the manufacture of a medicament for the treatment of diseases associated with platelet aggregation.

The diseases associated with platelet aggregation include, but are not limited to, e.g. thrombotic diseases, viral diseases having a hypercoagulable state, neoplastic diseases, coronary heart disease, stroke, hypertension, leukemia, disseminated intravascular coagulation (DIC) and the like.

EMBODIMENTS

The present invention is further and specifically explained by the following examples. However, these examples are merely used for illustrating the present invention, and they shall not be deemed to limit the protection scope of the present invention.

In the examples, the abbreviation MeOH represents methanol; EtOAc represents ethyl acetate; $Et_3N$ represents triethylamine; $Et_4NCl$ represents tetraethylammonium chloride; P.E. represents petroleum ether (having a boiling range of from 60 to 90° C.); $CDCl_3$ represents deuterated chloroform; DMSO-$d_6$ represents deuterated dimethyl sulphoxide; ADP represents adenosine diphosphate; AA represents arachidonic acid; TLC represent thin-layer chromatography; i-AmONO represents isoamyl nitrite; $Ac_2O$ represents acetic anhydride; $R_1SSR_1$ represents disulfides; EtOH represents ethanol.

$^1H$ NMR is measured with Varian Mercury 200 (200 MHz), Varian Mercury Plus 300 (300 MHz), Bruker 400 AMX (400 MHz) or Bruker 600 AMX (600 MHz) nuclear magnetic resonance apparatus, wherein s represents singlets; br s represents broadsinglets; d represents doublets; t represents triplets; q represents quartets; sextet represents sextets; heptet represents heptets; m represents multiplets; and Ar represents aryl.

I. Preparation Examples of Compounds

Example 1

Preparation of 2-amino-6-hydroxyl-9-(2',3',5'-tri-O-acetyl-β-D-ribofuranosyl)purine (2)

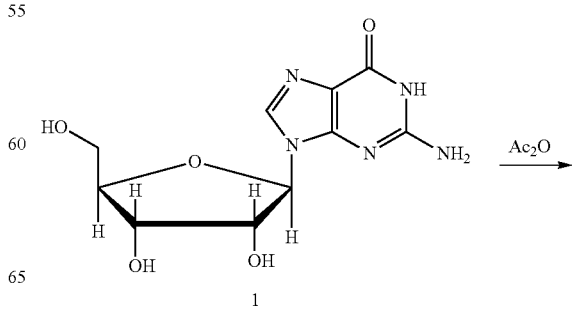

1

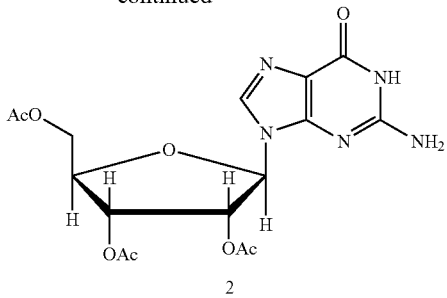

At room temperature, dried guanosine 1 (11.3 g, 40 mmol), triethylamine (22.9 mL, 158.4 mmol) and acetic anhydride (13.6 mL, 144 mmol) were respectively dissolved in 500 ml anhydrous acetonitrile, and 4-dimethylamino pyridine (366 mg, 3 mmol) was added therein. The resultant mixed solution was sharply stirred at room temperature for 30 min, and then continuously stirred for 10 min after 5 ml anhydrous methanol was added. The solvent was evaporated under reduced pressure, and the resultant solid was recrystallized with 180 mL isopropanol to obtain white crystals 2 (15.7 g, 96%), m.p 229-231° C.; $^1$H NMR (300 MHz, DMSO-$d_6$) δ 10.75 (1H, br s), 7.94 (1H, s), 6.55 (2H, br s), 5.98 (1H, d, J=4.8 Hz), 5.79 (1H, t, J=5.5 Hz), 5.59 (1H, t, J=5.5 Hz), 4.40-4.24 (3H, m), 2.11 (3H, s), 2.04 (3H, s), 2.03 (3H, s).

Example 2

Preparation of 2-amino-6-chloro-9-(2',3',5'-tri-O-acetyl-β-D-ribofuranosyl) purine (3)

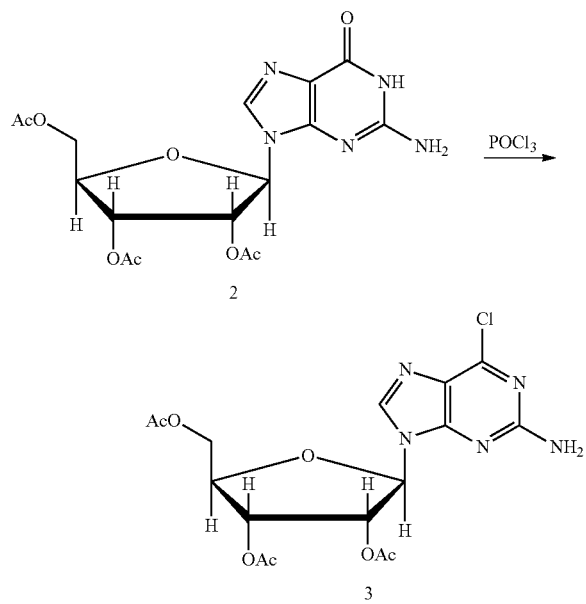

Anhydrous acetonitrile (15 mL) and anhydrous 1,2-dichloroethane (30 mL) were placed into a 100 ml three-necked bottle. While stirring at room temperature, 10.0 g (24.4 mmol) compound 2, 11.0 g (66.4 mmol) Et$_4$NCl and 16.8 g (10.0 mL, 109.6 mmol) POCl$_3$, and 4.78 g (5.0 mL, 35.1 mmol) N,N-dimethylaniline were successively added therein, and rapidly heated to reflux. After holding 20-25 min, the resultant mixed solution was slowly and dropwise added to brash ice and stirred, and 10 mL 1,2-dichloroethane was supplemented. After brash ice was completely dissolved, the resultant mixed solution was poured into a 250 mL separating funnel for separation. After the aqueous phase was extracted three times with 50 mL 1,2-dichloroethane, the organic phases were combined together and adjusted to a pH of 7 with cold 5% sodium carbonate solution, then a liquid separation was carried out. The organic phase was washed three times with 50 mL cold water, and dried over anhydrous MgSO$_4$, filtered and evaporated under reduced pressure to remove the solvent, and then 70 mL anhydrous ethanol was added to the residue which was recrystallized therefrom as a white crystal 3 (8.56 g, with a yield of 81.9%), m.p 155-156° C.; $^1$H NMR (600 MHz, CDCl$_3$) δ 7.88 (1H, s), 5.99 (1H, d, J=4.8 Hz), 5.93 (1H, t, J=4.9 Hz), 5.72 (1H, t, J=4.9 Hz), 5.27 (2H, br s), 4.35-4.44 (3H, m), 2.13 (3H, s), 2.09 (3H, s), 2.07 (3H, s).

The intermediate compound 4 was prepared according to the following reaction route.

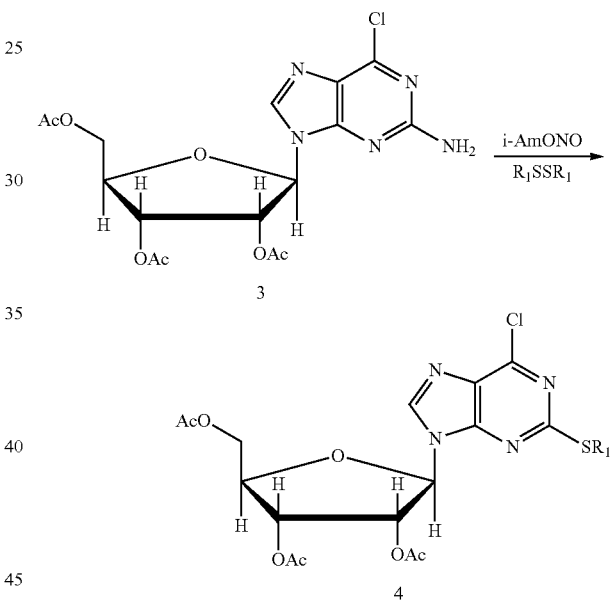

Example 3

Preparation of 2-methylthio-6-chloro-9-(2',3',5'-tri-O-acetyl-β-D-ribofuranosyl) purine (4a)

Compound 3 (2.5 g, 5.85 mmol) and dimethyl disulfide (29.25 mmol) were respectively added to 35 mL anhydrous acetonitrile, then nitrogen gas was fed to the mixed solution, and at room temperature, the mixed solution was stirred for 30 min, and then isoamyl nitrite (4.25 g, 36.3 mmol) was immediately added to the mixed solution. The resultant mixed solution was continuously stirred at room temperature for 10 min, and then transferred to an oil bath at 60° C., and heated for 4-8 hours. After it was detected with TLC (EtOAc-P.E., 1:1) that the starting materials disappeared, the solvent was evaporated under reduced pressure, and the residue was isolated by column chromatography (silica gel, EtOAc-P.E., 2:3, 1:1) to obtain a light yellow oily liquid 4a, with a yield of 66%; $^1$H NMR (300 MHz, CDCl$_3$): δ 8.09

(1H, s), 6.09 (1H, d, J=4.5 Hz), 5.97 (1H, t, J=5.4 Hz), 5.62 (1H, t, J=5.4 Hz), 4.45-4.43 (1H, m), 4.42-4.39 (1H, m), 4.32-4.26 (1H, m), 2.61 (3H, s), 2.12 (3H, s), 2.08 (3H, s), 2.06 (3H, s).

Example 4

Preparation of 2-ethylthio-6-chloro-9-(2',3',5'-tri-O-acetyl-β-D-ribofuranosyl) purine (4b)

The preparation method above-mentioned in Example 3 was used, except that dimethyl disulfide was replaced with diethyl disulfide, and the residue was isolated by column chromatography (silica gel, EtOAc-P.E., 2:3, 1:1) to obtain a light yellow liquid 4b, with a yield of 62%; $^1$H NMR (300 MHz, CDCl$_3$): δ 8.10 (1H, s), 6.09 (1H, d, J=4.5 Hz), 5.93 (1H, t, J=5.4 Hz), 5.59 (1H, t, J=5.4 Hz), 4.45-4.43 (1H, m), 4.42-4.40 (1H, m), 4.32-4.30 (1H, m), 3.21 (2H, q, J=7.3 Hz), 2.14 (3H, s), 2.09 (6H, s), 1.41 (3H, t, J=7.3 Hz).

Example 5

Preparation of 2-propylthio-6-chloro-9-(2',3',5'-tri-O-acetyl-β-D-ribofuranosyl) purine (4c)

The preparation method above-mentioned in Example 3 was used, except that dimethyl disulfide was replaced with dipropyl disulfide, and the residue was isolated by column chromatography (silica gel, EtOAc-P.E., 2:3, 1:1) to obtain a light yellow liquid 4c, with a yield of 57%; $^1$H NMR (600 MHz, DMSO-d$_6$): δ 8.69 (1H, s), 6.29 (1H, d, J=4.5 Hz), 6.01 (1H, t, J=5.4 Hz), 5.58 (1H, t, J=5.4), 4.42-4.40 (1H, m), 4.39-4.38 (1H, m), 4.25-4.22 (1H, m), 3.19 (2H, t, J=7.3 Hz), 2.11 (3H, s), 2.06 (3H, s), 1.97 (3H, s), 1.77-1.71 (2H, m), 1.01 (3H, t, J=7.3 Hz).

Example 6

Preparation of 2-isopropylthio-6-chloro-9-(2',3',5'-tri-oxy-acetyl-β-D-ribofuranosyl) purine (4d)

The preparation method above-mentioned in Example 3 was used, except that dimethyl disulfide was replaced with diisopropyl disulfide, and the residue was isolated by column chromatography (silica gel, EtOAc-P.E., 2:3, 1:1) to obtain a light yellow liquid 4d, with a yield of 43%; $^1$H NMR (300 MHz, CDCl$_3$): δ 8.10 (1H, s), 6.11 (1H, d, J=4.8 Hz), 5.90 (1H, t, J=5.4 Hz), 5.57 (1H, t, J=5.4 Hz), 4.44-4.42 (1H, m), 4.40-4.38 (1H, m), 4.33-4.28 (1H, m), 4.00 (1H, heptet, J=7.3 Hz), 2.13 (3H, s), 2.09 (3H, s), 2.08 (3H, s), 1.44 (6H, d, J=7.3 Hz).

Example 7

Preparation of 2-butylthio-6-chloro-9-(2',3',5'-tri-O-acetyl-β-D-ribofuranosyl) purine (4e)

The preparation method above-mentioned in Example 3 was used, except that dimethyl disulfide was replaced with dibutyl disulfide, and the residue was isolated by column chromatography (silica gel, EtOAc-P.E., 2:3, 1:1) to obtain a light yellow liquid 4e, with a yield of 50%; $^1$H NMR (600 MHz, CDCl$_3$): δ 8.11 (1H, s), 6.14 (1H, d, J=4.8 Hz), 5.89 (1H, t, J=5.4 Hz), 5.58 (1H, t, J=5.3), 4.45-4.43 (1H, m), 4.42-4.40 (1H, m), 4.34-4.31 (1H, m), 3.20 (2H, t, J=7.3), 2.13 (3H, s), 2.10 (3H, s), 2.08 (3H, s), 1.76-1.71 (2H, m), 1.51-1.45 (2H, m), 0.95 (3H, t, J=7.3 Hz).

The compound of the formula (I) or (I-1) (when R$_2$=R$_{2a}$ in the formula (I)) of the present invention was prepared according to the following reaction route.

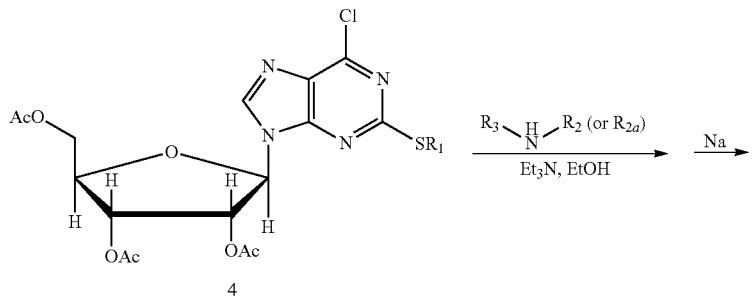

4

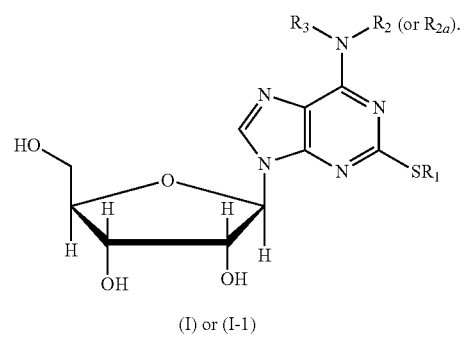

(I) or (I-1)

Example 8

Preparation of 2-propylthio-6-n-hexylamino-9-β-D-ribofuranosyl purine

Compound 4c (2 mmol) was dissolved in 20 mL anhydrous ethanol, and then triethylamine (1 mmol) and n-hexylamine (10 mmol) were added successively and refluxed for 8 hours. After it was detected with TLC (MeOH-EtOAc, 1:15, v/v) that the starting materials disappeared, a catalytic amount of the metal sodium (0.05 mmol) was added to remove the protecting group of acetyl. After it was monitored by TLC that the reaction was completed, the solvent was evaporated under reduced pressure, and the residue was isolated by column chromatography ($Et_3N$-neutralized silica gel, gradient elution, MeOH-EtOAc, 1:30, 1:15, v/v). Upon recrystallizing with methanol and washing with water, the title compound was obtained as white crystals with a yield of 84%, m.p 186-188° C.; $^1$H NMR (600 MHz, DMSO-$d_6$): δ 8.19 (1H, s), 7.92 (1H, br s), 5.80 (1H, d, J=6.0 Hz), 5.37 (1H, d, J=6.0 Hz), 5.13 (1H, d, J=4.8 Hz), 5.06 (1H, t, J=5.4 Hz), 4.58 (1H, ddd, J=5.6, 5.8, 6.0 Hz), 4.13 (1H, ddd, J=3.8, 4.8, 5.6 Hz), 3.92 (1H, ddd, J=3.8, 4.4, 5.4 Hz), 3.66-3.63 (1H, m), 3.55-3.52 (1H, m), 3.44 (2H, br s), 3.07 (2H, t, J=7.3 Hz), 1.72-1.67 (2H, m), 1.60-1.56 (2H, m), 1.28 (6H, m), 0.99 (3H, t, J=7.3 Hz), 0.86 (3H, t, J=6.5 Hz).

Example 9

Preparation of 2-ethylthio-6-cyclohexylamino-9-β-D-ribofuranosyl purine

The preparation method above-mentioned in Example 8 was used, except that the intermediate 4b reacted with cyclohexylamine for 10 hours; the residue was separated by column chromatography ($Et_3N$-neutralized silica gel, gradient elution, MeOH-EtOAc, 1:30, 1:15, v/v) and recrystallized with EtOAc, the title compound was obtained as white crystals with a yield of 80%, m.p 166-168° C.; $^1$H NMR (600 MHz, $CDCl_3$): δ 7.74 (1H, s), 6.10 (1H, br s), 5.76 (1H, d, J=6.7 Hz), 5.43 (1H, d, J=6.1 Hz), 5.19 (1H, d, J=4.8 Hz), 5.03 (1H, t, J=5.4 Hz), 4.43 (1H, br s), 4.29 (1H, br s), 4.11-4.05 (1H, m), 3.94-3.92 (1H, m), 3.76-3.74 (1H, m), 3.08 (1H, dt, J=7.3, 14.6 Hz), 2.94 (1H, dt, J=7.3, 14.6 Hz), 1.81-1.65 (9H, m), 1.34 (3H, t, J=7.3 Hz), 1.27-1.25 (2H, m).

Example 10

Preparation of 2-propylthio-6-cyclohexylamino-9-β-D-ribofuranosyl purine

The preparation method above-mentioned in Example 8 was used, except that the intermediate 4c reacted with cyclohexylamine for 7 hours; the residue was separated by column chromatography ($Et_3N$-neutralized silica gel, gradient elution, MeOH-EtOAc, 1:30, 1:15, v/v) and recrystallized with EtOAc, the title compound was obtained as white crystals with a yield of 82%, m.p 162-164° C.; $^1$H NMR (300 MHz, DMSO-$d_6$): δ 8.21 (1H, s), 7.72 (1H, br s), 5.81 (1H, d, J=5.9 Hz), 5.42 (1H, d, J=6.1 Hz), 5.18 (1H, d, J=4.8 Hz), 5.10 (1H, t, J=5.4 Hz), 4.59 (1H, ddd, J=5.0, 5.9, 6.1 Hz), 4.14 (1H, ddd, J=3.4, 4.8, 5.0 Hz), 3.94 (1H, ddd, J=3.4, 4.6, 6.0 Hz), 3.69-3.62 (1H, m), 3.58-3.51 (1H, m), 3.04 (2H, t, J=7.3 Hz), 1.90-1.87 (2H, m), 1.76-1.73 (2H, m), 1.71-1.28 (9H, m), 0.99 (3H, t, J=7.3 Hz).

Example 11

Preparation of 2-isopropylthio-6-cyclohexylamino-9-β-D-ribofuranosyl purine

The preparation method above-mentioned in Example 8 was used, except that the intermediate 4d reacted with cyclohexylamine for 9 hours; the residue was separated by column chromatography ($Et_3N$-neutralized silica gel, gradient elution, MeOH-EtOAc, 1:30, 1:15, v/v) and recrystallized with EtOAc, the title compound was obtained as white crystals with a yield of 77%, m.p 136-138° C.; $^1$H NMR (400 MHz, DMSO-$d_6$): δ 8.20 (1H, s), 7.72 (1H, br s), 5.80 (1H, d, J=5.8 Hz), 5.39 (1H, d, J=6.1 Hz), 5.15 (1H, d, J=4.8 Hz), 5.07 (1H, t, J=5.4 Hz), 4.57 (1H, ddd, J=5.6, 5.8, 6.1 Hz), 4.00 (1H, ddd, J=3.7, 4.7, 5.6 Hz), 3.91 (1H, ddd, J=3.5, 4.7, 6.1 Hz), 3.87-3.82 (1H, m), 3.66-3.61 (1H, m), 3.52 (1H, heptet, J=6.1 Hz), 1.88-1.86 (2H, m), 1.76-1.73 (2H, m), 1.63-1.60 (1H, m), 1.37 (6H, d, J=6.1 Hz), 1.32-1.11 (6H, m).

Example 12

Preparation of 2-butylthio-6-cyclohexylamino-9-β-D-ribofuranosyl purine

The preparation method above-mentioned in Example 8 was used, except that the intermediate 4e reacted with cyclohexylamine for 9 hours; the residue was separated by column chromatography ($Et_3N$-neutralized silica gel, gradient elution, MeOH-EtOAc, 1:30, 1:15, v/v) and recrystallized with EtOAc, the title compound was obtained as white crystals with a yield of 88%, m.p 138-140° C.; $^1$H NMR (400 MHz, DMSO-$d_6$): δ 8.20 (1H, s), 7.72 (1H, br s), 5.80 (1H, d, J=5.6 Hz), 5.40 (1H, d, J=5.8 Hz), 5.15 (1H, d, J=4.8 Hz), 5.08 (1H, t, J=5.4, 5.6 Hz), 4.57 (1H, ddd, J=4.9, 5.6, 5.8 Hz), 4.12 (1H, ddd, J=3.2, 4.5, 4.9 Hz), 4.03 (1H, br s), 3.91 (1H, ddd, J=3.2, 4.6, 6.0 Hz), 3.67-3.62 (1H, m), 3.56-3.50 (1H, m), 3.06 (2H, t, J=7.3 Hz), 1.89-1.87 (2H, m), 1.77-1.74 (2H, m), 1.68-1.61 (3H, m), 1.47-1.42 (2H, m), 1.38-1.11 (6H, m), 0.92 (3H, t, J=7.3 Hz).

Example 13

Preparation of 2-ethylthio-6-benzylamino-9-β-D-ribofuranosyl purine

The preparation method above-mentioned in Example 8 was used, except that the intermediate 4b reacted with benzylamine for 8 hours; the residue was separated by column chromatography ($Et_3N$-neutralized silica gel, gradient elution, MeOH-EtOAc, 1:50, 1:25, v/v) and recrystallized with EtOAc, the title compound was obtained as white crystals with a yield of 82%, m.p. 172-174° C.; $^1$H NMR: (600 MHz, DMSO-$d_6$): δ 8.51 (1H, br s), 8.24 (1H, s), 7.33-7.28 (4H, m), 7.21 (1H, t, J=7.0 Hz), 5.82 (1H, d, J=5.9 Hz), 5.39 (1H, d, J=6.1 Hz), 5.15 (1H, d, J=4.8 Hz), 5.04 (1H, t, J=5.4 Hz), 4.66 (2H, br s), 4.58 (1H, ddd, J=5.6, 5.9, 6.1 Hz), 4.12 (1H, ddd, J=3.4, 4.7, 5.6 Hz), 3.91 (1H, ddd, J=3.4, 4.7, 5.7 Hz), 3.65-3.62 (1H, m), 3.55-3.51 (1H, m), 3.00 (2H, q, J=7.3 Hz), 1.28 (3H, t, J=7.3 Hz).

Example 14

Preparation of 2-propylthio-6-benzylamino-9-β-D-ribofuranosyl purine

The preparation method above-mentioned in Example 8 was used, except that the intermediate 4c reacted with benzylamine for 8 hours; the residue was separated by column chromatography (Et$_3$N-neutralized silica gel, gradient elution, MeOH-EtOAc, 1:50, 1:25, v/v) and recrystallized with EtOAc, the title compound was obtained as white crystals with a yield of 79%, m.p 168-170° C.; $^1$H NMR: (600 MHz, DMSO-d$_6$): δ 8.51 (1H, br s), 8.24 (1H, s), 7.33-7.28 (4H, m), 7.21 (1H, t, J=7.0 Hz), 5.82 (1H, d, J=5.9 Hz), 5.39 (1H, d, J=6.1 Hz), 5.15 (1H, d, J=4.8 Hz), 5.04 (1H, t, J=5.4 Hz), 4.66 (2H, br s), 4.58 (1H, ddd, J=5.4, 5.7, 6.0 Hz), 4.12 (1H, ddd, J=3.2, 4.5, 5.4 Hz), 3.91 (1H, ddd, J=3.2, 4.3, 5.8 Hz), 3.65-3.62 (1H, in), 3.55-3.51 (1H, m), 3.00 (2H, q, J=7.3 Hz), 1.28 (3H, t, J=7.3 Hz).

Example 15

Preparation of 2-butylthio-6-benzylamino-9-β-D-ribofuranosyl purine

The preparation method above-mentioned in Example 8 was used, except that the intermediate 4e reacted with benzylamine for 8 hours; the residue was separated by column chromatography (Et$_3$N-neutralized silica gel, gradient elution, MeOH-EtOAc, 1:50, 1:25, v/v) and recrystallized with EtOAc, the title compound was obtained as white crystals with a yield of 80%, m.p 170-172° C.; $^1$H NMR (600 MHz, DMSO-d$_6$): δ 8.50 (1H, br s), 8.24 (1H, s), 7.28-7.31 (4H, m), 7.21 (1H, t, J=7.0 Hz), 5.81 (1H, d, J=5.9 Hz), 5.39 (1H, d, J=6.0 Hz), 5.14 (1H, d, J=4.8 Hz), 5.04 (1H, t, J=4.8 Hz), 4.67 (2H, br s), 4.59 (1H, ddd, J=5.5, 5.9, 6.1 Hz), 4.13 (1H, ddd, J=4.3, 4.7, 5.5 Hz), 3.92 (1H, ddd, J=3.6, 4.6, 5.4 Hz), 3.66-3.62 (1H, m), 3.55-3.51 (1H, m), 3.00 (2H, t, J=7.3 Hz), 1.59-1.54 (2H, m), 1.35-1.31 (2H, m) 0.89 (3H, t, J=7.3 Hz).

Example 16

Preparation of 2-ethylthio-6-(1-phenylethyl)amino-9-β-D-ribofuranosyl purine

The preparation method above-mentioned in Example 8 was used, except that the intermediate 4b reacted with 1-phenylethylamine for 8 hours; the residue was separated by column chromatography (Et$_3$N-neutralized silica gel, gradient elution, MeOH-EtOAc, 1:30, 1:15, v/v) and recrystallized with cyclohexane, the title compound was obtained as white crystals with a yield of 72%, m.p 84-86° C.; $^1$H NMR (600 MHz, DMSO-d$_6$): δ 8.40 (1H, br s), 8.24 (1H, s), 7.40 (2H, d, J=7.1 Hz), 7.30 (2H, t, J=7.5 Hz), 7.18 (1H, t, J=7.3 Hz), 5.80 (1H, d, J=5.9 Hz), 5.41 (1H, m), 5.38 (1H, d, J=6.1 Hz), 5.13 (1H, d, J=4.8 Hz), 5.05 (1H, t, J=5.4 Hz), 4.58 (1H, ddd, J=5.7, 5.9, 6.1 Hz), 4.12 (1H, ddd, J=3.7, 4.8, 5.7 Hz), 3.92 (1H, ddd, J=3.6, 4.2, 4.3 Hz), 3.64-3.62 (1H, m), 3.54-3.51 (1H, m), 2.98 (2H, q, J=7.3 Hz), 1.53 (3H, d, J=6.8 Hz), 1.21 (3H, t, J=7.3 Hz).

Example 17

Preparation of 2-propylthio-6-([4-methoxylbenzyl]amino)-9-β-D-ribofuranosyl purine The preparation method above-mentioned in Example 8 was used, except that the intermediate 4c reacted with 4-methoxylbenzylamine for 11 hours; the residue was separated by column chromatography (Et$_3$N-neutralized silica gel, gradient elution, MeOH-EtOAc, 1:30, 1:15, v/v) and recrystallized with EtOAc, the title compound was obtained as white crystals with a yield of 81%, m.p 152-154° C.; $^1$H NMR (200 MHz, DMSO-d$_6$): δ 8.46 (1H, br s), 8.25 (1H, s), 7.26 (2H, d, J=8.6 Hz), 6.86 (2H, d, J=8.6 Hz), 5.84 (1H, d, J=6.0 Hz), 5.47 (1H, d, J=6.0 Hz), 5.22 (1H, d, J=4.8 Hz), 5.14 (1H, t, J=5.4 Hz), 4.61 (2H, br s), 4.58 (1H, ddd, J=5.8, 6.0, 6.1 Hz), 4.16 (1H, ddd, J=3.4, 4.8, 5.8 Hz), 3.95 (1H, ddd, J=3.4, 3.9, 4.6 Hz), 3.70 (3H, s), 3.64-3.61 (1H, m), 3.60-3.55 (1H, m), 3.02 (2H, t, J=7.3 Hz), 1.54-1.72 (2H, m), 0.92 (3H, t, J=7.3 Hz).

Example 18

Preparation of 2-methylthio-6-phenylethylamino-9-β-D-ribofuranosyl purine

The preparation method above-mentioned in Example 8 was used, except that the intermediate 4a reacted with 2-phenylethylamine for 9 hours; the residue was separated by column chromatography (Et$_3$N-neutralized silica gel, gradient elution, MeOH-EtOAc, 1:30, 1:15, v/v) and recrystallized with EtOAc, the title compound was obtained as white crystals with a yield of 85%, m.p 156-158° C.; $^1$H NMR (300 MHz, DMSO-d$_6$): δ 8.22 (1H, s), 8.02 (1H, br s), 7.30-7.25 (3H, m), 7.20-7.17 (2H, m), 5.83 (1H, d, J=5.5 Hz), 5.45 (1H, d, J=5.5 Hz), 5.20 (1H, d, J=4.8 Hz), 5.08 (1H, t, J=5.4 Hz), 4.60 (1H, ddd, J=5.4, 5.5, 5.6 Hz), 4.14 (1H, ddd, J=3.4, 4.2, 4.6 Hz), 3.92 (1H, ddd, J=3.4, 4.5, 4.9 Hz), 3.68-3.65 (2H, m), 3.57-3.51 (2H, m), 2.90 (2H, t, J=7.6 Hz), 2.50 (3H, s).

Example 19

Preparation of 2-ethylthio-6-phenylethylamino-9-β-D-ribofuranosyl purine

The preparation method above-mentioned in Example 8 was used, except that the intermediate 4b reacted with 2-phenylethylamine for 9 hours; the residue was separated by column chromatography (Et$_3$N-neutralized silica gel, gradient elution, MeOH-EtOAc, 1:30, 1:15, v/v) and recrystallized with EtOAc, the title compound was obtained as white crystals with a yield of 84%, m.p 130-132° C.; $^1$H NMR (300 MHz, DMSO-d$_6$): δ 8.23 (1H, s), 8.02 (1H, br s), 7.32-7.26 (3H, m), 7.24-7.17 (2H, m), 5.84 (1H, d, J=5.9 Hz), 5.45 (1H, d, J=6.2 Hz), 5.21 (1H, d, J=4.8 Hz), 5.11 (1H, t, J=5.5 Hz), 4.60 (1H, ddd, J=5.6, 5.7, 6.1 Hz), 4.16 (1H, ddd, J=3.5, 4.8, 5.6 Hz), 3.95 (1H, ddd, J=3.5, 4.3, 4.8 Hz), 3.67-3.65 (2H, m), 3.58-3.46 (2H, m), 3.11 (2H, q, J=7.3 Hz), 2.92 (2H, t, J=7.0 Hz), 1.34 (3H, t, J=7.3 Hz).

Example 20

Preparation of 2-propylthio-6-phenylethylamino-9-β-D-ribofuranosyl purine

The preparation method above-mentioned in Example 8 was used, except that the intermediate 4c reacted with 2-phenylethylamine for 9 hours; the residue was separated by column chromatography (Et$_3$N-neutralized silica gel, gradient elution, MeOH-EtOAc, 1:30, 1:15, v/v) and recrystallized with EtOAc, the title compound was obtained as white crystals with a yield of 80%, m.p 110-112° C.; $^1$H NMR (300 MHz, DMSO-d$_6$): δ 8.22 (1H, s), 8.03 (1H, br s), 7.32-7.26 (3H, m), 7.24-7.17 (2H, m), 5.82 (1H, d, J=5.9 Hz), 5.44 (1H, d, J=6.2 Hz), 5.18 (1H, d, J=4.8 Hz), 5.10 (1H, t, J=5.4 Hz), 4.59 (1H, ddd, J=5.4, 5.9, 6.2 Hz), 4.14 (1H, ddd, J=3.5, 4.2, 4.8 Hz), 3.93 (1H, ddd, J=3.5, 4.6, 5.2

Hz), 3.69-3.64 (2H, m), 3.62-3.50 (2H, m), 3.09 (2H, t, J=7.3 Hz), 2.91 (2H, t, J=7.0 Hz), 1.74-1.67 (2H, m), 0.97 (3H, t, J=7.3 Hz).

Example 21

Preparation of 2-butylthio-6-phenylethylamino-9-β-D-ribofuranosyl purine

The preparation method above-mentioned in Example 8 was used, except that the intermediate 4e reacted with 2-phenylethylamine for 9 hours; the residue was separated by column chromatography (Et$_3$N-neutralized silica gel, gradient elution, MeOH-EtOAc, 1:30, 1:15, v/v) and recrystallized with EtOAc, the title compound was obtained as white crystals with a yield of 81%, m.p 124-126° C.; $^1$H NMR (400 MHz, DMSO-d$_6$): δ 8.20 (1H, s), 8.01 (1H, br s), 7.31-7.26 (3H, m), 7.25-7.18 (2H, m), 5.80 (1H, d, J=5.6 Hz), 5.41 (1H, d, J=6.1 Hz), 5.16 (1H, d, J=4.8 Hz), 5.07 (1H, t, J=5.4 Hz), 4.57 (1H, ddd, J=5.6, 5.7, 6.1 Hz), 4.12 (1H, ddd, J=3.7, 4.7, 5.7 Hz), 3.92 (1H, ddd, J=3.7, 4.6, 5.8 Hz), 3.68-3.64 (2H, m), 3.62-3.50 (2H, m), 3.10 (2H, t, J=7.3 Hz), 2.91 (2H, t, J=7.5 Hz), 1.70-1.63 (2H, m), 1.45-1.36 (2H, m), 0.89 (3H, t, J=7.3 Hz).

Example 22

Preparation of 2-methylthio-6-([4-methoxylphenyl-ethyl]-amino)-9-β-D-ribofuranosyl purine The preparation method above-mentioned in Example 8 was used, except that the intermediate 4a reacted with 4-methoxylphenylethylamine for 12 hours; the residue was separated by column chromatography (Et$_3$N-neutralized silica gel, gradient elution, MeOH-EtOAc, 1:30, 1:15, v/v) and recrystallized with EtOAc, the title compound was obtained as white crystals with a yield of 82%, m.p 152-154° C.; $^1$H NMR (300 MHz, DMSO-d$_6$): δ 8.24 (1H, s), 7.97 (1H, br s), 7.16 (2H, d, J=7.9 Hz), 6.85 (2H, d, J=8.0 Hz), 5.87 (1H, d, J=5.9 Hz), 5.47 (1H, d, J=5.9 Hz), 5.24 (1H, d, J=4.8 Hz), 5.12 (1H, t, J=5.4 Hz), 4.63 (1H, ddd, J=5.4, 5.8, 6.2 Hz), 4.19 (1H, ddd, J=3.5, 4.8, 5.4 Hz), 3.97 (1H, ddd, J=3.5, 4.3, 4.6 Hz), 3.70 (3H, s), 3.65-3.66 (2H, m), 3.53-3.49 (2H, m), 2.85 (2H, t, J=7.1 Hz), 2.52 (3H, s).

Example 23

Preparation of 2-ethylthio-6-([4-methoxylphenyl-ethyl]amino)-9-β-D-ribofuranosyl purine The preparation method above-mentioned in Example 8 was used, except that the intermediate 4b reacted with 4-methoxylphenylethylamine for 9 hours; the residue was separated by column chromatography (Et$_3$N-neutralized silica gel, gradient elution, MeOH-EtOAc, 1:30, 1:15, v/v) and recrystallized with EtOAc, the title compound was obtained as white crystals with a yield of 81%, m.p 140-142° C.; $^1$H NMR (200 MHz, DMSO-d$_6$): δ 8.25 (1H, s), 7.99 (1H, br s), 7.16 (2H, d, J=8.0 Hz), 6.85 (2H, d, J=8.0 Hz), 5.86 (1H, d, J=5.9 Hz), 5.47 (1H, d, J=5.9 Hz), 5.22 (1H, d, J=4.8 Hz), 5.13 (1H, t, J=5.4 Hz), 4.63 (1H, ddd, J=5.4, 5.9, 6.2 Hz), 4.17 (1H, ddd, J=3.4, 4.8, 5.4 Hz), 3.98 (1H, ddd, J=3.4, 4.2, 4.6 Hz), 3.70 (3H, s), 3.66-3.60 (2H, m), 3.54-3.44 (2H, m), 3.12 (2H, q, J=7.3 Hz), 2.85 (2H, t, J=7.1 Hz), 1.35 (3H, t, J=7.3 Hz).

Example 24

Preparation of 2-propylthio-6-([4-methoxylphenyl-ethyl]amino)-9-β-D-ribofuranosyl purine The preparation method above-mentioned in Example 8 was used, except that the intermediate 4c reacted with 4-methoxylphenylethylamine for 12 hours; the residue was separated by column chromatography (Et$_3$N-neutralized silica gel, gradient elution, MeOH-EtOAc, 1:30, 1:15, v/v) and recrystallized with EtOAc, the title compound was obtained as white crystals with a yield of 83%, m.p 170-172° C.; $^1$H NMR (300 MHz, DMSO-d$_6$): δ 8.21 (1H, s), 8.00 (1H, br s), 7.15 (2H, d, J=8.0 Hz), 6.85 (2H, d, J=8.0 Hz), 5.81 (1H, d, J=5.9 Hz), 5.42 (1H, d, J=5.9 Hz), 5.17 (1H, d, J=4.8 Hz), 5.08 (1H, t, J=5.4 Hz), 4.59 (1H, ddd, J=5.3, 5.8, 5.8 Hz), 4.13 (1H, br s), 3.92 (1H, ddd, J=3.5, 4.6, 5.6 Hz), 3.71 (3H, s), 3.64-3.62 (2H, m), 3.55-3.51 (2H, m), 3.09 (2H, t, J=7.3 Hz), 2.84 (2H, t, J=7.5 Hz), 1.74-1.64 (2H, m), 0.98 (3H, t, J=7.3 Hz).

Example 25

Preparation of 2-butylthio-6-([4-methoxylphenyl-ethyl]amino)-9-β-D-ribofuranosyl purine The preparation method above-mentioned in Example 8 was used, except that the intermediate 4e reacted with 4-methoxylphenylethylamine for 12 hours; the residue was separated by column chromatography (Et$_3$N-neutralized silica gel, gradient elution, MeOH-EtOAc, 1:30, 1:15, v/v) and recrystallized with EtOAc, the title compound was obtained as white crystals with a yield of 80%, m.p 122-124° C.; $^1$H NMR (400 MHz, DMSO-d$_6$): δ 8.21 (1H, s), 7.98 (1H, br s), 7.15 (2H, d, J=8.0 Hz), 6.85 (2H, d, J=8.2 Hz), 5.80 (1H, d, J=5.8 Hz), 5.41 (1H, d, J=5.9 Hz), 5.16 (1H, d, J=4.8 Hz), 5.07 (1H, t, J=4.9 Hz), 4.58 (1H, ddd, J=5.2, 5.8, 6.1 Hz), 4.13 (1H, ddd, J=3.8, 4.8, 5.2 Hz), 3.92 (1H, ddd, J=3.8, 4.3, 4.6 Hz), 3.71 (3H, s), 3.67-3.64 (2H, m), 3.53-3.518 (2H, m), 3.10 (2H, t, J=7.3 Hz), 2.84 (2H, t, J=7.1 Hz), 1.70-1.63 (2H, m), 1.46-1.37 (2H, m), 0.89 (3H, t, J=7.3 Hz).

Example 26

Preparation of 2-ethylthio-6-([3-methoxylphenyl-ethyl]amino)-9-β-D-ribofuranosyl purine The preparation method above-mentioned in Example 8 was used, except that the intermediate 4b reacted with 3-methoxylphenylethylamine for 11 hours; the residue was separated by column chromatography (Et$_3$N-neutralized silica gel, gradient elution, MeOH-EtOAc, 1:30, 1:15, v/v) and recrystallized with EtOAc, the title compound was obtained as white crystals with a yield of 84%, m.p 110-112° C.; $^1$H NMR (300 MHz, DMSO-d$_6$): δ 8.22 (1H, s), 8.01 (1H, br s), 7.20 (1H, t, J=8.0 Hz), 6.81-6.75 (3H, m), 5.82 (1H, d, J=5.9 Hz), 5.43 (1H, d, J=6.1 Hz), 5.18 (1H, d, J=4.8 Hz), 5.08 (1H, t, J=5.4 Hz), 4.59 (1H, ddd, J=5.4, 5.7, 6.1 Hz), 4.14 (1H, ddd, J=3.7, 4.8, 5.4 Hz), 3.93 (1H, ddd, J=3.7, 4.5, 4.6 Hz), 3.72 (3H, s), 3.70-3.63 (2H, m), 3.58-3.53 (2H, m), 3.11 (2H, q, J=7.3 Hz), 2.89 (2H, t, J=7.6 Hz), 1.34 (3H, t, J=7.3 Hz).

Example 27

Preparation of 2-propylthio-6-([3-methoxylphenyl-ethyl]amino)-9-β-D-ribofuranosyl purine The preparation method above-mentioned in Example 8 was used, except that the intermediate 4c reacted with 3-methoxylphenylethylamine for 11 hours; the residue was separated by column chromatography (Et$_3$N-neutralized silica gel, gradient elution, MeOH-EtOAc, 1:30, 1:15, v/v) and recrystallized with EtOAc, the title compound was obtained as white crystals with a yield of 76%, imp 120-122° C.; $^1$H NMR (300 MHz, DMSO-d$_6$) δ 8.22 (1H, s), 8.01 (1H, br s), 7.20 (1H, t, J=8.0 Hz), 6.82-6.75 (3H, m), 5.81 (1H, d, J=6.0 Hz), 5.43 (1H, d, J=6.1 Hz), 5.18 (1H, d, J=4.8 Hz), 5.09 (1H, t, J=5.5 Hz), 4.60 (1H, ddd, J=5.7, 5.9, 6.1 Hz), 4.13 (1H, ddd, J=3.4, 4.8, 5.7 Hz), 3.92 (1H, ddd, J=3.3, 4.0, 4.5 Hz), 3.72 (3H, s), 3.67-3.62 (2H, m), 3.57-3.50 (2H, m), 3.09 (2H, t, J=7.3 Hz), 2.89 (2H, t, J=7.1 Hz), 1.74-1.64 (2H, m), 0.98 (3H, t, J=7.3 Hz).

Example 28

Preparation of 2-ethylthio-6,6-(dibutylamino)-9-β-D-ribofuranosyl purine

The preparation method above-mentioned in Example 8 was used, except that the intermediate 4b reacted with n-dibutylamine for 14 hours; the residue was separated by column chromatography (Et$_3$N-neutralized silica gel, gradient elution, EtOAc-petroleum ether, 1:10, 1:1, v/v) and recrystallized with n-hexane, the title compound was obtained as white crystals with a yield of 58%, m.p 152-154° C.; $^1$H NMR (400 MHz, DMSO-d$_6$): δ 8.24 (1H, s), 5.82 (1H, d, J=6.0 Hz), 5.41 (1H, d, J=6.2 Hz), 5.17 (1H, d, J=4.8 Hz), 5.07 (1H, t, J=5.2 Hz), 4.55 (1H, ddd, J=5.3, 6.0, 6.2 Hz), 4.12 (1H, ddd, J=3.4, 4.9, 5.3 Hz), 3.92 (1H, ddd, J=3.4, 4.6, 6.2 Hz), 3.67-3.62 (2H, m), 3.62-3.49 (4H, m), 3.12-3.04 (2H, m), 1.66-1.56 (4H, m), 1.39-1.34 (4H, m), 1.32 (3H, t, J=7.3 Hz), 0.92 (6H, t, J=6.4 Hz).

Example 29

Preparation of 2-ethylthio-6-(2-thienylethyl)amino-9-β-D-ribofuranosyl purine

The preparation method above-mentioned in Example 8 was used, except that the intermediate 4b reacted with 2-thienylethylamine for 4 hours; the residue was separated by column chromatography (Et$_3$N-neutralized silica gel, MeOH-EtOAc, 1:20, v/v) and recrystallized with EtOAc, the title compound was obtained as white crystals with a yield of 80%, m.p 142-144° C.; $^1$H NMR (400 MHz, DMSO-d$_6$): δ 8.23 (1H, s), 8.09 (1H, br s), 7.32 (1H, dd, J=1.08, 1.12 Hz), 6.96-6.91 (2H, m), 5.81 (1H, d, J=5.92 Hz), 5.42 (1H, d, J=6.08 Hz), 5.17 (1H, d, J=4.56 Hz), 5.07 (1H, t, J=6.09 Hz), 4.58 (1H, q, J=5.63, 5.75 Hz) 4.12 (1H, q, J=4.71, 4.50 Hz), 3.91 (1H, q, J=3.79, 3.79 Hz), 3.71-3.63 (3H, m), 3.56-3.50 (1H, m), 3.15-3.07 (4H, m), 1.33 (3H, t, J=7.24 Hz).

Example 30

Preparation of 2-propylthio-6-(2-thienylethyl)amino-9-β-D-ribofuranosyl purine

The preparation method above-mentioned in Example 8 was used, except that the intermediate 4c reacted with 2-thienylethylamine for 5 hours; the residue was separated by column chromatography (Et$_3$N-neutralized silica gel, MeOH-EtOAc, 1:15, v/v) and recrystallized with n-hexane, the title compound was obtained as white crystals with a yield of 70%, $^1$H NMR (400 MHz, DMSO-d$_6$): δ 8.22 (1H, s), 8.09 (1H, br s), 7.32 (1H, dd, J=1.11, 1.11 Hz), 6.96-6.91 (2H, m), 5.80 (1H, d, J=5.92 Hz), 5.41 (1H, d, J=5.96 Hz), 5.17 (1H, d, J=3.89 Hz), 5.07 (1H, t, J=6.22 Hz), 4.58 (1H, q, J=5.63, 5.75 Hz), 4.12 (1H, m), 3.91 (1H, q, J=3.69, 3.69 Hz), 3.71-3.62 (3H, m), 3.55-3.51 (1H, m), 3.15-3.076 (4H, m), 1.69 (2H, sextet, J=7.29), 0.97 (3H, t, J=7.29 Hz).

Example 31

Preparation of 2-ethylthio-6-(3-phenylpropyl)amino-9-β-D-ribofuranosyl purine

The preparation method above-mentioned in Example 8 was used, except that the intermediate 4b reacted with 3-phenyl-1-propylamine for 4 hours; the residue was separated by column chromatography (Et$_3$N-neutralized silica gel, MeOH-EtOAc, 1:20, v/v) and recrystallized with methanol, the title compound was obtained as white crystals with a yield of 80%, m.p 180-182° C.; $^1$H NMR (400 MHz, DMSO-d$_6$): δ 8.22 (1H, s), 8.03 (1H, br s), 7.29-7.15 (5H, m), 5.81 (1H, d, J=5.98 Hz), 5.41 (1H, d, J=6.09 Hz), 5.17 (1H, d, J=4.83 Hz), 5.07 (1H, t, J=5.05 Hz), 4.58 (1H, q, J=5.86, 5.97 Hz), 4.12 (1H, q, J=4.60, 4.71 Hz), 3.91 (1H, q, J=3.91, 3.79 Hz), 3.66-3.61 (1H, m), 3.55-3.46 (3H, m), 3.02 (2H, q, J=7.91, 7.36 Hz), 2.63 (2H, t, J=7.47 Hz), 1.89 (2H, q, J=7.47 Hz), 1.29 (3H, t, J=7.24 Hz).

Example 32

Preparation of 2-ethylthio-6-(4-phenylbutyl)amino-9-β-D-ribofuranosyl purine

The preparation method above-mentioned in Example 8 was used, except that the intermediate 4b reacted with 4-phenyl-1-butylamine for 5 hours; the residue was separated by column chromatography (Et$_3$N-neutralized silica gel, MeOH-EtOAc, 1:20, v/v) and recrystallized with methanol, the title compound was obtained as white crystals with a yield of 80%, m.p 146-148° C.; $^1$H NMR (400 MHz, DMSO-d$_6$): δ 8.20 (1H, s), 7.98 (1H, br s), 7.28-7.14 (5H, m), 5.81 (1H, d, J=5.85 Hz), 5.42 (1H, d, J=6.06 Hz), 5.18 (1H, d, J=4.70 Hz), 5.08 (1H, t, J=5.17 Hz), 4.59 (1H, q, J=5.69 Hz, 5.85 Hz), 4.12 (1H, q, J=4.49, 4.60 Hz), 3.91 (1H, q, J=3.97, 3.86 Hz), 3.67-3.61 (1H, m), 3.56-3.47 (m, 3H), 3.05 (2H, dd, J=2.03, 1.88 Hz), 2.60 (2H, t, J=7.05 Hz), 1.89 (2H, q, J=7.47 Hz), 1.61 (4H, br), 1.31 (3H, t, J=7.24 Hz).

Example 33

Preparation of 2-ethylthio-6-(2-furylmethyl)amino-9-β-D-ribofuranosyl purine

The preparation method above-mentioned in Example 8 was used, except that the intermediate 4b reacted with 2-furylmethylamine for 5 hours; the residue was separated by column chromatography (Et$_3$N-neutralized silica gel, MeOH-EtOAc, 1:15, v/v) and recrystallized with a mixed solvent of ethyl acetate and petroleum ether, the title compound was obtained as white crystals with a yield of 75%, m.p 190-192° C.; $^1$H NMR (400 MHz, DMSO-d$_6$): δ 8.41 (1H, br s), 8.26 (1H, s), 7.55 (1H, s), 6.37 (1H, m), 6.22 (1H, m), 5.82 (1H, d, J=5.92 Hz), 5.43 (1H, d, J=6.07 Hz), 5.17 (1H, d, J=4.80 Hz), 5.05 (1H, t, J=5.50 Hz), 4.65-4.57 (3H, m), 4.12 (1H, q, J=4.51, 4.66 Hz), 3.92 (1H, q, J=3.67, 3.67 Hz), 3.67-3.62 (1H, m), 3.56-3.50 (1H, m), 3.07 (2H, dd, J=2.11, 1.97 Hz), 1.30 (3H, t, J=7.19 Hz).

Example 34

Preparation of 2-ethylthio-6-(2-tetrahydrofurylmethyl)amino-9-β-D-ribofuranosyl purine The preparation method above-mentioned in Example 8 was used, except that the intermediate 4b reacted with 2-tetrahydrofurylmethylamine for 5 hours; the residue was separated by column chromatography (Et$_3$N-neutralized silica gel, MeOH-EtOAc, 1:15, v/v) and recrystallized with methanol, the title compound was obtained as white crystals with a yield of 82%, m.p 89-91° C.; $^1$H NMR (400 MHz, DMSO-d$_6$): δ 8.23 (1H, s), 7.85 (1H, br s), 5.81 (1H, d, J=5.93 Hz), 5.42 (1H, d, J=6.21 Hz), 5.17 (1H, d, J=4.80 Hz), 5.06 (1H, t, J=5.36 Hz), 4.58 (1H, q, J=5.78, 5.78 Hz), 4.13 (1H, q, J=4.65, 4.93 Hz), 4.09 (1H, m), 3.92 (1H, q, J=3.81, 3.81 Hz), 3.77 (1H, q, J=7.05, 6.35 Hz), 3.67-3.59 (2H, m), 3.56-3.50 (2H, m), 3.45 (1H, t, J=5.93 Hz), 3.09-3.05 (2H, m), 1.93-1.74 (3H, m), 1.67-1.61 (1H, m), 1.33 (3H, t, J=7.34 Hz).

II. Preparation Examples of Formulations

Formulation Example 1

Preparation of Injection 40.0 g of a compound of Example 19 was sufficiently mixed with 22.56 g of disodium hydrogen phosphate, 0.519 g of sodium dihydrogen phosphate, 2 g of sodium metabisulfite, 5 g of benzyl alcohol, 5 g of glycerol. Water for injection was added to 1000 mL, to obtain the injection containing the compound of the present invention.

Formulation Example 2

Preparation of Tablets 5 g of a compound of Example 18, 12 g of lactose, 8 g of corn starch, 0.2 g of magnesium stearate and 0.02 g of methyl cellulose were mixed together and compressed according to the conventional methods to obtain 100 tablets.

III. Bioactivity Assay

The inventor conducted the anti-platelet aggregation activity screening for the compounds of the present invention, carried out the anti-platelet aggregation test by using the blood platelet which was closed to human physiological state and was not washed with water, and conducted the activity test of the in vitro anti-platelet aggregation induced by ADP, and also the activity test of the in vitro anti-platelet aggregation induced by AA (arachidonic acid) for some compounds. The present invention firstly discloses the activity test of the in vitro anti-platelet aggregation induced by AA conducted with said type of compounds. The results show that the compounds of the present invention have a notable anti-platelet aggregation activity.
Evaluation of Anti-Platelet Aggregation Activity The anti-platelet aggregation test of the compounds was conducted by the aggregometer (Model 400VS, Chrono-Log, Haverston, Pa.) from Chrono-Log Corp. ADP, AA (arachidonic acid), DMSO and trisodium citrate were purchased from Sigama.
1. Test Method:

The whole blood was obtained from healthy volunteers who did not take any anti-platelet medicines within 2 weeks. The fasting venous blood of the subjects was collected, and placed into a 50 mL sampling tube containing 3.8% sodium citrate, and mixed homogeneously in a ratio of 1:9 (v/v) for anticoagulation, and centrifugalized at 300 rpm/min for 20 min.

The supernatant was taken to obtain platelet-rich blood plasma (PRP). The residual blood was then centrifugalized at 900 rpm/min for 10 min, and the supernatant fluid was taken to obtain platelet-poverty blood plasma (PPP). The analysis of platelet aggregation was conducted by using the aggregometer (Chrono-Log Corp.), wherein PRP and PPP were respectively added to two turbidimetric tubes. In the aggregometer, platelet-poverty blood plasma (PPP) was used as the control group. DMSO was used as the negative control. The turbidimetric tubes were incubated at 37° C. for 3 min. The PRP was stirred with a stirring rod at 900 rpm/min for 10-20 s, and the inductive agent ADP (10 uM) or AA (0.5 mM) was added to PRP, and start to record the aggregated wave patterns. The chart speed of the recorder (Model 707, Chrono-Log, Haverston, Pa., USA) was set up to be 1 cm min$^{-1}$, and the aggregation reaction was recorded for not less than 3 min. Finally, the apparatus automatically delineated the aggregation curve and calculated the results, i.e. maximum platelet aggregation rate. When the platelet aggregation was lower than 50% of the control group, the IC$_{50}$ of the compound was calculated.
2. Test Results: See Table 1

TABLE 1

Activities of the in vitro anti-platelet aggregation of the compounds of the present invention

| Compounds | IC$_{50}$ (ADP, μM) | IC$_{50}$ (AA, μM) |
| --- | --- | --- |
| Example 8 | 102 | |
| Example 9 | 104 | |
| Example 10 | 151 | |
| Example 11 | 187 | |
| Example 12 | 83 | |
| Example 13 | 176 | |
| Example 14 | 216 | |
| Example 15 | 202 | |
| Example 16 | 197 | |
| Example 17 | 181 | |
| Example 18 | 36 | 3 |
| Example 19 | 29 | 30 |
| Example 20 | 52 | 44 |
| Example 21 | 59 | >300 |
| Example 22 | 153 | |
| Example 23 | 89 | |
| Example 24 | 267 | |
| Example 25 | 93 | |
| Example 26 | 38 | >300 |
| Example 27 | 69 | |

The results of the in vitro anti-platelet aggregation tests have showed that all the compounds have the effect of in vitro inhibiting ADP-induced platelet aggregation in various extents; and at the same time, a part of the compounds have a notable effect on in vitro inhibiting AA (arachidonic acid)-induced platelet aggregation.

The invention claimed is:
1. The following compounds or pharmaceutically acceptable salts thereof:
2-propylthio-6-n-hexylamino-9-β-D-ribofuranosyl purine;
2-ethylthio-6-cyclohexylamino-9-β-D-ribofuranosyl purine;
2-propylthio-6-cyclohexylamino-9-β-D-ribofuranosyl purine;

2-isopropylthio-6-cyclohexylamino-9-β-D-ribofuranosyl purine;
2-butylthio-6-cyclohexylamino-9-β-D-ribofuranosyl purine;
2-ethylthio-6-benzylamino-9-β-D-ribofuranosyl purine;
2-propylthio-6-benzylamino-9-β-D-ribofuranosyl purine;
2-butylthio-6-benzylamino-9-β-D-ribofuranosyl purine;
2-ethylthio-6-(1-phenylethyl)amino-9-β-D-ribofuranosyl purine;
2-propylthio-6-([4-methoxylbenzyl]amino)-9-β-D-ribofuranosyl purine;
2-methylthio-6-phenylethylamino-9-β-D-ribofuranosyl purine;
2-ethylthio-6-phenylethylamino-9-β-D-ribofuranosyl purine;
2-propylthio-6-phenylethylamino-9-β-D-ribofuranosyl purine;
2-butylthio-6-phenylethylamino-9-β-D-ribofuranosyl purine;
2-methylthio-6-([4-methoxylphenylethyl]amino)-9-β-D-ribofuranosyl purine;
2-ethylthio-6-([4-methoxylphenylethyl]amino)-9-β-D-ribofuranosyl purine;
2-propylthio-6-([4-methoxylphenylethyl]amino)-9-β-D-ribofuranosyl purine;
2-butylthio-6-([4-methoxylphenylethyl]amino)-9-β-D-ribofuranosyl purine;
2-ethylthio-6-([3-methoxylphenylethyl]amino)-9-β-D-ribofuranosyl purine;
2-propylthio-6-([3-methoxylphenylethyl]amino)-9-β-D-ribofuranosyl purine;
2-ethylthio-6,6-(dibutylamino)-9-β-D-ribofuranosyl purine;
2-propylthio-6-(2-thienylethyl)amino-9-β-D-ribofuranosyl purine;
2-ethylthio-6-(3-phenylpropyl)amino-9-β-D-ribofuranosyl purine;
2-ethylthio-6-(4-phenylbutyl)amino-9-β-D-ribofuranosyl purine;
2-ethylthio-6-(2-furylmethyl)amino-9-β-D-ribofuranosyl purine; and
2-ethylthio-6-(2-tetrahydrofurylmethyl)amino-9-β-D-ribofuranosyl purine.

2. A method for the treatment of diseases associated with platelet aggregation in a mammal in need thereof, comprising administering an effective amount of the compound of the formula (I) or a pharmaceutically acceptable salt thereof,

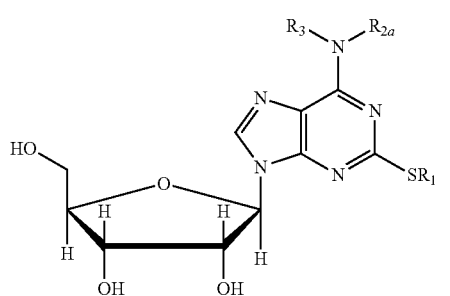
(I)

wherein
$R_1$ represents an unsubstituted or $R_4$-substituted $C_1$-$C_8$ hydrocarbyl, or an unsubstituted or $R_5$-substituted 5- to 6-membered cyclic group;
$R_2$ represents an unsubstituted or $R_5$-substituted $C_3$-$C_8$ saturated or unsaturated aliphatic hydrocarbyl, an unsubstituted or $R_5$-substituted $C_3$-$C_8$ alicyclic group, an unsubstituted or $R_6$-substituted $C_6$-$C_{10}$ aryl-$C_1$-$C_4$ alkyl, an unsubstituted or $R_6$-substituted 5- to 10-membered heterocyclyl-$C_1$-$C_4$ alkyl, or an unsubstituted or $R_6$-substituted 5- to 10-membered heteroaryl-$C_1$-$C_4$ alkyl;
$R_3$ represents H or $R_2$;
$R_4$ represents halogen, $C_1$-$C_4$ alkyl, $C_1$-$C_4$ alkoxyl, halogenated $C_1$-$C_4$ alkyl, halogenated $C_1$-$C_4$ alkoxyl, hydroxyl, hydroxyl $C_1$-$C_4$ alkyl, carboxyl, nitro, cyano, $C_1$-$C_4$ alkylthio, or $C_1$-$C_4$ alkyl-CO—;
$R_5$ represents $C_1$-$C_4$ alkyl, $C_1$-$C_4$ alkoxyl, hydroxyl, hydroxyl $C_1$-$C_4$ alkyl, carboxyl, nitro, cyano, $C_1$-$C_4$ alkylthio or $C_1$-$C_4$ alkyl-CO—; and
$R_6$ represents halogen, $C_1$-$C_4$ alkyl, $C_1$-$C_4$ alkoxyl, hydroxyl, hydroxyl $C_1$-$C_4$ alkyl, carboxyl, nitro, cyano, $C_1$-$C_4$ alkylthio, or $C_1$-$C_4$ alkyl-CO—.

3. The method according to claim 2, wherein $R_1$ represents an unsubstituted or $R_4$-substituted $C_1$-$C_6$ alkyl; $R_2$ represents an unsubstituted or $R_5$-substituted $C_3$-$C_6$ alkyl, an unsubstituted or $R_5$-substituted $C_3$-$C_6$ cycloalkyl, an unsubstituted or $R_6$-substituted 5- to 6-membered heteroaryl-$C_1$-$C_4$ alkyl, an unsubstituted or $R_6$-substituted phenyl-$C_1$-$C_4$ alkyl, or an unsubstituted or $R_6$-substituted 5- to 6-membered heterocyclyl-$C_1$-$C_4$ alkyl; and $R_3$ represents H or $C_3$-$C_6$ alkyl; wherein $R_4$ represents halogen, $C_1$-$C_4$ alkyl, $C_1$-$C_4$ alkoxyl, halogenated $C_1$-$C_4$ alkyl, halogenated $C_1$-$C_4$ alkoxyl, or $C_1$-$C_4$ alkylthio; $R_5$ is selected from the group consisting of $C_1$-$C_4$ alkyl, $C_1$-$C_4$ alkoxyl, hydroxyl, hydroxyl $C_1$-$C_4$ alkyl, carboxyl, nitro, cyano, $C_1$-$C_4$ alkylthio or $C_1$-$C_4$ alkyl-CO—; and $R_6$ is selected from the group consisting of halogen, $C_1$-$C_4$ alkyl, $C_1$-$C_4$ alkoxyl, hydroxyl, hydroxyl $C_1$-$C_4$ alkyl, carboxyl, nitro, cyano, $C_1$-$C_4$ alkylthio, and $C_1$-$C_4$ alkyl-CO—.

4. The method according to claim 3, wherein $R_1$ represents $C_1$-$C_6$ alkyl; $R_2$ represents $C_3$-$C_6$ alkyl, $C_5$-$C_6$ cycloalkyl, an unsubstituted or $R_6$-substituted phenyl-$C_1$-$C_4$ alkyl, an unsubstituted or $R_6$-substituted 5- to 6-membered heteroaryl-$C_1$-$C_4$ alkyl, or an unsubstituted or $R_6$-substituted 5- to 6-membered heterocyclyl-$C_1$-$C_4$ alkyl, wherein $R_6$ is selected from the group consisting of $C_1$-$C_4$ alkyl, $C_1$-$C_4$ alkoxyl and $C_1$-$C_4$ alkylthio.

5. The method according to claim 3, wherein $R_1$ represents methyl, ethyl, n-propyl, isopropyl or butyl; $R_2$ represents n-hexyl, cyclohexyl, 1-phenylethyl, 2-phenylethyl, 3-phenylpropyl, 4-phenylbutyl, methoxylphenylethyl, 2-thienylethyl, furylmethyl, or tetrahydrofurylmethyl.

6. The method according to claim 2, wherein the disease associated with platelet aggregation is selected from the group consisting of thrombotic diseases, viral diseases having a hypercoagulable state, neoplastic diseases, coronary heart disease, stroke, hypertension, leukemia and disseminated intravascular coagulation (DIC).

* * * * *

UNITED STATES PATENT AND TRADEMARK OFFICE
CERTIFICATE OF CORRECTION

PATENT NO. : 9,493,502 B2  
APPLICATION NO. : 13/981694  
DATED : November 15, 2016  
INVENTOR(S) : Du et al.

It is certified that error appears in the above-identified patent and that said Letters Patent is hereby corrected as shown below:

On the Title Page

Item (30), Foreign Application Priority Data:
Please correct "(CN)..........2011 1 0028107" to read -- (CN)...........2011 1 0028107.3 --

Signed and Sealed this
Twentieth Day of June, 2017

Joseph Matal
*Performing the Functions and Duties of the
Under Secretary of Commerce for Intellectual Property and
Director of the United States Patent and Trademark Office*